(12) United States Patent
Field et al.

(10) Patent No.: US 10,357,328 B2
(45) Date of Patent: Jul. 23, 2019

(54) MARKING DEVICE WITH RETRACTABLE CANNULA

(75) Inventors: Steven E. Field, Grand Rapids, MI (US); Ryan L. Goosen, Coopersville, MI (US); Richard E. Davis, Grand Rapids, MI (US); Richard M. Chesbrough, Bloomfield Hills, MI (US)

(73) Assignee: Bard Peripheral Vascular, Inc. and Bard Shannon Limited, Franklin Lakes, NJ (US)

( * ) Notice: Subject to any disclaimer, the term of this patent is extended or adjusted under 35 U.S.C. 154(b) by 1809 days.

(21) Appl. No.: 10/907,906

(22) Filed: Apr. 20, 2005

(65) Prior Publication Data

US 2006/0241411 A1     Oct. 26, 2006

(51) Int. Cl.
    *A61B 90/00*          (2016.01)

(52) U.S. Cl.
    CPC ...... *A61B 90/39* (2016.02); *A61B 2090/0801* (2016.02); *A61B 2090/3908* (2016.02); *A61B 2090/3987* (2016.02)

(58) Field of Classification Search
    CPC .......... A61M 37/0069; A61B 17/3468; A61B 2019/5487; A61B 2090/0801; A61B 2090/3987; A61B 2019/3908; A61B 90/39; A61D 1/025
    USPC ........ 604/61; 600/424, 431, 130, 7; 128/897
    See application file for complete search history.

(56) References Cited

U.S. PATENT DOCUMENTS

| | | | |
|---|---|---|---|
| 2,192,270 A | 3/1940 | McGowan | |
| 2,481,408 A | 9/1949 | Fuller et al. | |
| 2,832,888 A | 4/1958 | Houston | |
| 2,899,362 A | 8/1959 | Sieger, Jr. et al. | |
| 2,907,327 A | 10/1959 | White | |

(Continued)

FOREIGN PATENT DOCUMENTS

| | | |
|---|---|---|
| DE | 1029528 B | 5/1958 |
| EP | 0146699 A1 | 7/1985 |

(Continued)

OTHER PUBLICATIONS

Press release for Biopsys Ethicon Endo-Surgery (Europe) GmbH; The Mammotome Vacuum Biopsy System. From: http://www.medicine-news.com/articles/devices/mammotome.html. 3 pages.

(Continued)

*Primary Examiner* — Jennifer Dieterle
*Assistant Examiner* — Helene Bor

(57) ABSTRACT

A marking device according to one embodiment of the invention comprises a handle, a cannula having a cannula distal end and slidably mounted to the handle, and a stylet having a stylet distal end and slidably mounted to the handle in the cannula. The stylet distal end is spaced proximally of the cannula distal end to form a marker recess that receives an imaging marker. The marking device further comprises an actuator operably coupled to the cannula to effect retraction of the cannula into the handle following implantation of the imaging marker. The imaging marker can be implanted by advancing the stylet relative to the cannula to eject the imaging marker from the marker recess, or the cannula can be retracted relative to the stylet to expose the imaging marker.

15 Claims, 19 Drawing Sheets

(56) References Cited

U.S. PATENT DOCUMENTS

| | | | |
|---|---|---|---|
| 3,005,457 A | 10/1961 | Millman | |
| 3,128,744 A * | 4/1964 | Jefferts et al. | 119/215 |
| 3,341,417 A | 9/1967 | Sinaiko | |
| 3,402,712 A * | 9/1968 | Eisenhand | 604/61 |
| 3,516,412 A | 6/1970 | Ackerman | |
| 3,593,343 A | 7/1971 | Viggers | |
| 3,757,781 A | 9/1973 | Smart | |
| 3,818,894 A | 6/1974 | Wichterle et al. | |
| 3,820,545 A * | 6/1974 | Jefferts | 606/117 |
| 3,823,212 A | 7/1974 | Chvapil | |
| 3,921,632 A | 11/1975 | Bardani | |
| 4,005,699 A | 2/1977 | Bucalo | |
| 4,007,732 A | 2/1977 | Kvavle et al. | |
| 4,041,931 A | 8/1977 | Elliot et al. | |
| 4,086,914 A | 5/1978 | Moore | |
| 4,103,690 A | 8/1978 | Harris | |
| 4,105,030 A | 8/1978 | Kercso | |
| 4,127,774 A | 11/1978 | Gillen | |
| 4,172,449 A | 10/1979 | LeRoy et al. | |
| 4,197,846 A | 4/1980 | Bucalo | |
| 4,217,889 A | 8/1980 | Radovan et al. | |
| 4,276,885 A | 7/1981 | Tickner et al. | |
| 4,294,241 A | 10/1981 | Miyata | |
| 4,298,998 A | 11/1981 | Naficy | |
| 4,331,654 A | 5/1982 | Morris | |
| 4,347,234 A | 8/1982 | Wahlig et al. | |
| 4,390,018 A | 6/1983 | Zukowski | |
| 4,400,170 A * | 8/1983 | McNaughton et al. | 604/62 |
| 4,401,124 A | 8/1983 | Guess et al. | |
| 4,405,314 A | 9/1983 | Cope | |
| 4,428,082 A | 1/1984 | Naficy | |
| 4,438,253 A | 3/1984 | Casey et al. | |
| 4,442,843 A | 4/1984 | Rasor et al. | |
| 4,470,160 A | 9/1984 | Cavon | |
| 4,487,209 A | 12/1984 | Mehl | |
| 4,545,367 A | 10/1985 | Tucci | |
| 4,549,560 A | 10/1985 | Andis | |
| 4,582,061 A | 4/1986 | Fry | |
| 4,582,640 A | 4/1986 | Smestad et al. | |
| 4,588,395 A | 5/1986 | Lemelson | |
| 4,597,753 A * | 7/1986 | Turley | 604/61 |
| 4,647,480 A | 3/1987 | Ahmed | |
| 4,655,226 A | 4/1987 | Lee | |
| 4,661,103 A | 4/1987 | Harman | |
| 4,682,606 A | 7/1987 | DeCaprio | |
| 4,693,237 A | 9/1987 | Hoffman et al. | |
| 4,718,433 A | 1/1988 | Feinstein | |
| 4,740,208 A | 4/1988 | Cavon | |
| 4,762,128 A | 8/1988 | Rosenbluth | |
| 4,813,062 A | 3/1989 | Gilpatrick | |
| 4,820,267 A | 4/1989 | Harman | |
| 4,832,680 A | 5/1989 | Haber et al. | |
| 4,832,686 A | 5/1989 | Anderson | |
| 4,847,049 A | 7/1989 | Yamamoto | |
| 4,863,470 A | 9/1989 | Carter | |
| 4,870,966 A | 10/1989 | Dellon et al. | |
| 4,874,376 A | 10/1989 | Hawkins, Jr. | |
| 4,889,707 A | 12/1989 | Day et al. | |
| 4,909,250 A | 3/1990 | Smith | |
| 4,931,059 A | 6/1990 | Markham | |
| 4,938,763 A | 7/1990 | Dunn et al. | |
| 4,950,234 A | 8/1990 | Fujioka et al. | |
| 4,950,665 A | 8/1990 | Floyd | |
| 4,963,150 A | 10/1990 | Brauman | |
| 4,970,298 A | 11/1990 | Silver et al. | |
| 4,989,608 A | 2/1991 | Ratner | |
| 4,994,013 A | 2/1991 | Suthanthiran et al. | |
| 4,994,028 A | 2/1991 | Leonard et al. | |
| 5,012,818 A | 5/1991 | Joishy | |
| 5,013,090 A | 5/1991 | Matsuura | |
| 5,018,530 A | 5/1991 | Rank et al. | |
| 5,035,891 A | 7/1991 | Runkel et al. | |
| 5,059,197 A | 10/1991 | Urie et al. | |
| 5,081,997 A | 1/1992 | Bosley, Jr. et al. | |
| 5,108,421 A | 4/1992 | Fowler | |
| 5,120,802 A | 6/1992 | Mares et al. | |
| 5,125,413 A | 6/1992 | Baran | |
| 5,137,928 A | 8/1992 | Erbel et al. | |
| 5,141,748 A | 8/1992 | Rizzo | |
| 5,147,295 A * | 9/1992 | Stewart | A61M 37/0069 604/61 |
| 5,147,307 A | 9/1992 | Gluck | |
| 5,147,631 A | 9/1992 | Glajch et al. | |
| 5,162,430 A | 11/1992 | Rhee et al. | |
| 5,163,896 A | 11/1992 | Suthanthiran et al. | |
| 5,195,540 A | 3/1993 | Shiber | |
| 5,197,482 A | 3/1993 | Rank et al. | |
| 5,197,846 A | 3/1993 | Uno et al. | |
| 5,199,441 A | 4/1993 | Hogle | |
| 5,201,704 A | 4/1993 | Ray | |
| 5,219,339 A * | 6/1993 | Saito | 604/198 |
| 5,221,269 A | 6/1993 | Miller et al. | |
| 5,231,615 A | 7/1993 | Endoh | |
| 5,234,426 A | 8/1993 | Rank et al. | |
| 5,236,410 A | 8/1993 | Granov et al. | |
| 5,242,759 A | 9/1993 | Hall | |
| 5,250,026 A | 10/1993 | Ehrlich et al. | |
| 5,271,961 A | 12/1993 | Mathiowitz et al. | |
| 5,273,532 A * | 12/1993 | Niezink et al. | 604/62 |
| 5,280,788 A | 1/1994 | Janes et al. | |
| 5,281,197 A | 1/1994 | Arias et al. | |
| 5,281,408 A | 1/1994 | Unger | |
| 5,282,781 A | 2/1994 | Liprie | |
| 5,284,479 A | 2/1994 | de Jong | |
| 5,289,831 A | 3/1994 | Bosley | |
| 5,290,310 A | 3/1994 | Makower et al. | |
| 5,312,435 A | 5/1994 | Nash et al. | |
| 5,320,100 A | 6/1994 | Herweck et al. | |
| 5,320,613 A | 6/1994 | Houge et al. | |
| 5,328,955 A | 7/1994 | Rhee et al. | |
| 5,334,216 A | 8/1994 | Vidal et al. | |
| 5,334,381 A | 8/1994 | Unger | |
| 5,344,640 A | 9/1994 | Deutsch et al. | |
| 5,353,804 A | 10/1994 | Kornberg et al. | |
| 5,354,623 A | 10/1994 | Hall | |
| 5,358,514 A | 10/1994 | Schulman et al. | |
| 5,360,416 A | 11/1994 | Ausherman et al. | |
| 5,366,756 A | 11/1994 | Chesterfield et al. | |
| 5,368,030 A | 11/1994 | Zinreich et al. | |
| 5,388,588 A | 2/1995 | Nabai et al. | |
| 5,394,875 A | 3/1995 | Lewis et al. | |
| 5,395,319 A | 3/1995 | Hirsch et al. | |
| 5,405,402 A | 4/1995 | Dye et al. | |
| 5,409,004 A | 4/1995 | Sloan | |
| 5,417,708 A | 5/1995 | Hall et al. | |
| 5,422,730 A | 6/1995 | Barlow et al. | |
| 5,425,366 A | 6/1995 | Reinhardt et al. | |
| 5,431,639 A | 7/1995 | Shaw | |
| 5,433,204 A | 7/1995 | Olson | |
| 5,449,560 A | 9/1995 | Antheunis et al. | |
| 5,451,406 A | 9/1995 | Lawin et al. | |
| 5,458,643 A | 10/1995 | Oka et al. | |
| 5,460,182 A | 10/1995 | Goodman et al. | |
| 5,469,847 A | 11/1995 | Zinreich et al. | |
| 5,475,052 A | 12/1995 | Rhee et al. | |
| 5,490,521 A | 2/1996 | Davis et al. | |
| 5,494,030 A | 2/1996 | Swartz et al. | |
| 5,499,989 A | 3/1996 | LaBash | |
| 5,507,807 A | 4/1996 | Shippert | |
| 5,508,021 A | 4/1996 | Grinstaff et al. | |
| 5,514,085 A | 5/1996 | Yoon | |
| 5,522,896 A | 6/1996 | Prescott | |
| 5,538,726 A | 7/1996 | Order | |
| 5,542,915 A | 8/1996 | Edwards et al. | |
| 5,545,180 A | 8/1996 | Le et al. | |
| 5,549,560 A | 8/1996 | Van de Wijdeven | |
| 5,567,413 A | 10/1996 | Klaveness et al. | |
| RE35,391 E | 12/1996 | Brauman | |
| 5,580,568 A | 12/1996 | Greff et al. | |
| 5,585,112 A | 12/1996 | Unger et al. | |
| 5,611,352 A | 3/1997 | Kobren et al. | |
| 5,626,611 A | 5/1997 | Liu et al. | |
| 5,628,781 A | 5/1997 | Williams et al. | |
| 5,629,008 A | 5/1997 | Lee | |

(56) References Cited

U.S. PATENT DOCUMENTS

| | | |
|---|---|---|
| 5,636,255 A | 6/1997 | Ellis |
| 5,643,246 A | 7/1997 | Leeb et al. |
| 5,646,146 A | 7/1997 | Faarup et al. |
| 5,651,772 A * | 7/1997 | Arnett ............... A61M 25/0631 604/164.01 |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,682 A | 12/1997 | Thompson |
| 5,702,716 A | 12/1997 | Dunn et al. |
| 5,716,981 A | 2/1998 | Hunter et al. |
| 5,747,060 A | 5/1998 | Sackler et al. |
| 5,749,887 A | 5/1998 | Heske et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,810,884 A | 9/1998 | Kim |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,830,222 A | 11/1998 | Makower |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,976,146 A | 11/1999 | Ogawa et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,166,079 A | 12/2000 | Follen et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 * | 2/2001 | Davis et al. ................ 604/61 |
| 6,190,353 B1 | 2/2001 | Makower et al. |
| 6,200,258 B1 | 3/2001 | Slater et al. |
| 6,203,507 B1 | 3/2001 | Wadsworth et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,405,733 B1 | 6/2002 | Fogarty et al. |
| 6,409,742 B1 | 6/2002 | Fulton, III et al. |
| 6,403,758 B1 | 7/2002 | Loomis |
| 6,419,621 B1 | 7/2002 | Sioshansi et al. |
| 6,424,857 B1 | 7/2002 | Henrichs et al. |
| 6,425,903 B1 | 7/2002 | Voegele |
| 6,427,081 B1 | 7/2002 | Burbank et al. |

(56) References Cited

U.S. PATENT DOCUMENTS

| | | |
|---|---|---|
| 6,436,030 B2 | 8/2002 | Rehil |
| 6,447,524 B1 | 9/2002 | Knodel et al. |
| 6,447,527 B1 | 9/2002 | Thompson et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,511,650 B1 | 1/2003 | Eiselt et al. |
| 6,537,193 B1 | 3/2003 | Lennox |
| 6,540,981 B2 | 4/2003 | Klaveness et al. |
| 6,544,185 B2 | 4/2003 | Montegrande |
| 6,544,231 B1 | 4/2003 | Palmer et al. |
| 6,544,269 B2 | 4/2003 | Osborne et al. |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,626,899 B2 | 9/2003 | Houser et al. |
| 6,628,982 B1 | 9/2003 | Thomas et al. |
| 6,629,947 B1 | 10/2003 | Sahatjian et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,659,933 B2 | 12/2003 | Asano |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,881,226 B2 | 4/2005 | Corbitt, Jr. et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,958,044 B2 | 10/2005 | Burbank et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,041,047 B2 | 5/2006 | Gellman et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,135,978 B2 | 11/2006 | Gisselberg et al. |
| 7,160,258 B2 | 1/2007 | Imran et al. |
| 7,172,549 B2 | 2/2007 | Slater et al. |
| 7,189,206 B2 | 3/2007 | Quick et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,280,865 B2 | 10/2007 | Adler |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,329,414 B2 | 2/2008 | Fisher et al. |
| 7,407,054 B2 | 8/2008 | Seiler et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 * | 8/2009 | Chesbrough ........... A61B 19/54 604/63 |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,668,582 B2 | 2/2010 | Sirimanne et al. |
| 7,670,350 B2 | 3/2010 | Selis |
| 7,783,336 B2 | 8/2010 | Macfarlane et al. |
| 7,819,819 B2 | 10/2010 | Quick et al. |
| 7,844,319 B2 | 11/2010 | Susil et al. |
| 7,877,133 B2 | 1/2011 | Burbank et al. |
| 7,914,553 B2 | 3/2011 | Ferree |
| 8,011,508 B2 | 9/2011 | Seiler et al. |
| 8,128,641 B2 | 3/2012 | Wardle |
| 8,306,602 B2 | 11/2012 | Sirimanne et al. |
| 8,320,993 B2 | 11/2012 | Sirimanne et al. |
| 8,320,994 B2 | 11/2012 | Sirimanne et al. |
| 8,334,424 B2 | 12/2012 | Szypka |
| 8,361,082 B2 | 1/2013 | Jones et al. |
| 8,442,623 B2 | 5/2013 | Nicoson et al. |
| 8,454,629 B2 | 6/2013 | Sells |
| 8,579,931 B2 | 11/2013 | Chesbrough et al. |
| 8,626,269 B2 | 1/2014 | Jones et al. |
| 8,626,270 B2 | 1/2014 | Burbank et al. |
| 8,639,315 B2 | 1/2014 | Burbank et al. |
| 8,668,737 B2 | 3/2014 | Corbitt, Jr. |
| 8,680,498 B2 | 3/2014 | Corbitt |
| 9,237,937 B2 | 1/2016 | Burbank et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0044969 A1 | 4/2002 | Harden et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082517 A1 | 6/2002 | Klein |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0177776 A1 | 11/2002 | Crawford Kellar et al. |
| 2002/0188195 A1 | 12/2002 | Mills |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |

(56) References Cited

U.S. PATENT DOCUMENTS

| | | |
|---|---|---|
| 2003/0040766 A1* | 2/2003 | Werner ............ A61B 17/3468 606/187 |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0044311 A1 | 3/2004 | Espositio et al. |
| 2004/0059341 A1 | 3/2004 | Gellman et al. |
| 2004/0068312 A1 | 4/2004 | Sigg et al. |
| 2004/0073107 A1 | 4/2004 | Sioshansi et al. |
| 2004/0073284 A1 | 4/2004 | Bates et al. |
| 2004/0097981 A1 | 5/2004 | Sells |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0153074 A1 | 8/2004 | Bojarski et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236212 A1 | 11/2004 | Jones et al. |
| 2004/0236213 A1 | 11/2004 | Jones et al. |
| 2004/0253185 A1 | 12/2004 | Herweck et al. |
| 2004/0265371 A1 | 12/2004 | Looney et al. |
| 2005/0019262 A1 | 1/2005 | Chernomorsky et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0112151 A1 | 5/2005 | Horng |
| 2005/0113659 A1 | 5/2005 | Pothier et al. |
| 2005/0119562 A1 | 6/2005 | Jones et al. |
| 2005/0142161 A1 | 6/2005 | Freeman et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0216018 A1 | 9/2005 | Sennett |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0116573 A1 | 6/2006 | Field et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0033280 A1 | 2/2008 | Lubock et al. |
| 2008/0039819 A1 | 2/2008 | Jones et al. |
| 2008/0091120 A1 | 4/2008 | Fisher |
| 2008/0097199 A1 | 4/2008 | Mullen |
| 2008/0121242 A1 | 5/2008 | Revie et al. |
| 2008/0188768 A1 | 8/2008 | Zarins et al. |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0093714 A1 | 4/2009 | Chesbrough et al. |
| 2009/0131825 A1 | 5/2009 | Burbank et al. |
| 2009/0171198 A1 | 7/2009 | Jones et al. |
| 2010/0298696 A1 | 11/2010 | Field et al. |
| 2011/0184280 A1 | 7/2011 | Jones et al. |
| 2012/0078092 A1 | 3/2012 | Jones et al. |
| 2012/0116215 A1 | 5/2012 | Jones et al. |
| 2012/0215230 A1 | 8/2012 | Lubock et al. |
| 2013/0144157 A1 | 6/2013 | Jones et al. |
| 2013/0281847 A1 | 10/2013 | Jones et al. |
| 2013/0310686 A1 | 11/2013 | Jones et al. |
| 2014/0058258 A1 | 2/2014 | Chesbrough et al. |
| 2014/0094698 A1 | 4/2014 | Burbank et al. |
| 2014/0114186 A1 | 4/2014 | Burbank et al. |
| 2014/0142696 A1 | 5/2014 | Corbitt, Jr. |
| 2014/0243675 A1 | 8/2014 | Burbank et al. |
| 2015/0051477 A1 | 2/2015 | Jones et al. |
| 2015/0164610 A1 | 6/2015 | Field et al. |
| 2016/0120510 A1 | 5/2016 | Burbank et al. |
| 2016/0128797 A1 | 5/2016 | Burbank et al. |
| 2016/0199150 A1 | 7/2016 | Field et al. |
| 2017/0042664 A1 | 2/2017 | Corbitt, Jr. |
| 2017/0100203 A1 | 4/2017 | Field et al. |
| 2017/0119492 A1 | 5/2017 | Chesbrough et al. |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| FR | 2853521 A1 | 10/2004 |
| GB | 708148 | 4/1954 |
| JP | 02131757 A | 5/1990 |

(56) References Cited

FOREIGN PATENT DOCUMENTS

| | | |
|---|---|---|
| JP | 2006516468 A | 7/2006 |
| JP | 2007537017 A | 12/2007 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2005112787 A2 | 12/2005 |
| WO | 2006012630 A2 | 2/2006 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Johnson & Johnson: Breast Biopsy (minimally invasive): Surgical Technique: Steps in the Mamotome Surgical Procedure. From http://www.jnjgateway.com. 3 pages.
Johnson & Johnson: New Minimally Invasive Breast Biopsy Device Receives Marketing Clearance in Canada; Aug. 6, 1999. From http://www.jnjgateway.com. 4 pages.
Johnson & Johnson: Mammotome Hand Held Receives FDA Marketing Clearance for Minimally Invasive Breast Biopises; Sep. 1, 1999. From From http://www.jnjgateway.com. 5 pages.
Johnson & Johnson: The Mammotome Breast Biopsy System. From: http://www.breastcareinfo.com/aboutm.htm. 6 pages.
Cook Incorporated: Emoblization and Occlusion. From: www.cookgroup.com 6 pages.
Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.
International Search Report for PCT/US2009/000945 dated Jul. 16, 2009.
Written Opinion of the International Searching Authority for PCT/US2009/000945 dated Jul. 16, 2009.
International Search Report for PCT/US2007/016902 dated Feb. 28, 2008.
International Search Report for PCT/US2007/016902 dated Feb. 4, 2009.
Written Opinion of the International Searching Authority for PCT/US2007/016902 dated Feb. 4, 2009.
International Search Report for PCT/US2007016918 dated Nov. 26, 2007.
Written Opinion of the International Searching Authority for PCT/US2007016918 dated Feb. 4, 2009.
Collagen—Definitions from Dictionary. com.
Fibrous—Definitions from Dictionary.com.
Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.
H. J. Gent, M.D., et al., Stereotaxic Needle Localization and Cytological Diagnosis of Occult Breast Lesions, Annals of Surgery, Nov. 1986, pp. 580-584, vol. 204—No. 5.
Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.
Fucci, V., et al., "Large Bowel Transit Times Using Radioopaque Markers in Normal Cats", J. of Am. Animal Hospital Assn., Nov.-Dec. 1995 31 (6) 473-477.
Schindlbeck, N.E., et al., "Measurement of Colon Transit Time", J. of Gastroenterology, No. 28, pp. 399-404, 1990.
Shiga, et al., Preparation of Poly(D, L-lactide) and Copoly(lactide-glycolide) Microspheres of Uniform Size, J. Pharm. Pharmacol. 1996 48:891-895.
Eiselt, P. et al, "Development of Technologies Aiding Large—Tissue Engineering", Biotechnol. Prog., vol. 14, No. 1, pp. 134-140, 1998.
Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.
Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.
Shah, et al. (Polyethylene Glycol as a Binder for Tablets, vol. 66, No. 11, Nov. 1977, Journal of Pharmaceutical Sciences).
Crook, et al. (Prostate Motion During Standard Radiotherapy as Assessed by Fiducial Markers, 1995, Radiotherapy and Oncology 37:35-42.).
Zmora, et al. (Tailoring the pore architecture in 3-D alginate scaffolds by controlling the freezing regime during fabrication, 2001, Elsevier Science Ltd.).
Madihally, et al. (Porous chitosan scaffolds for tissue engineering, 1998, Elsevier Science Ltd.).

\* cited by examiner

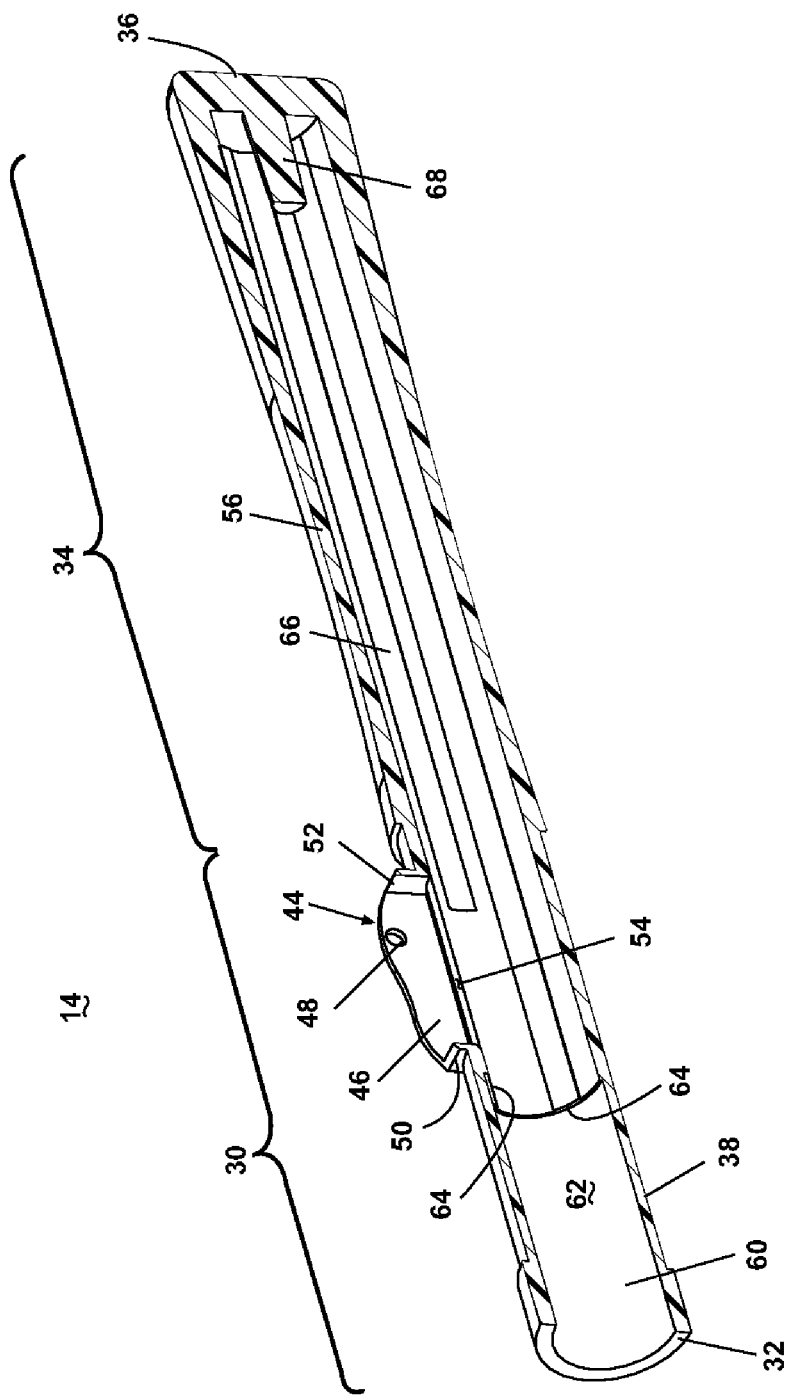

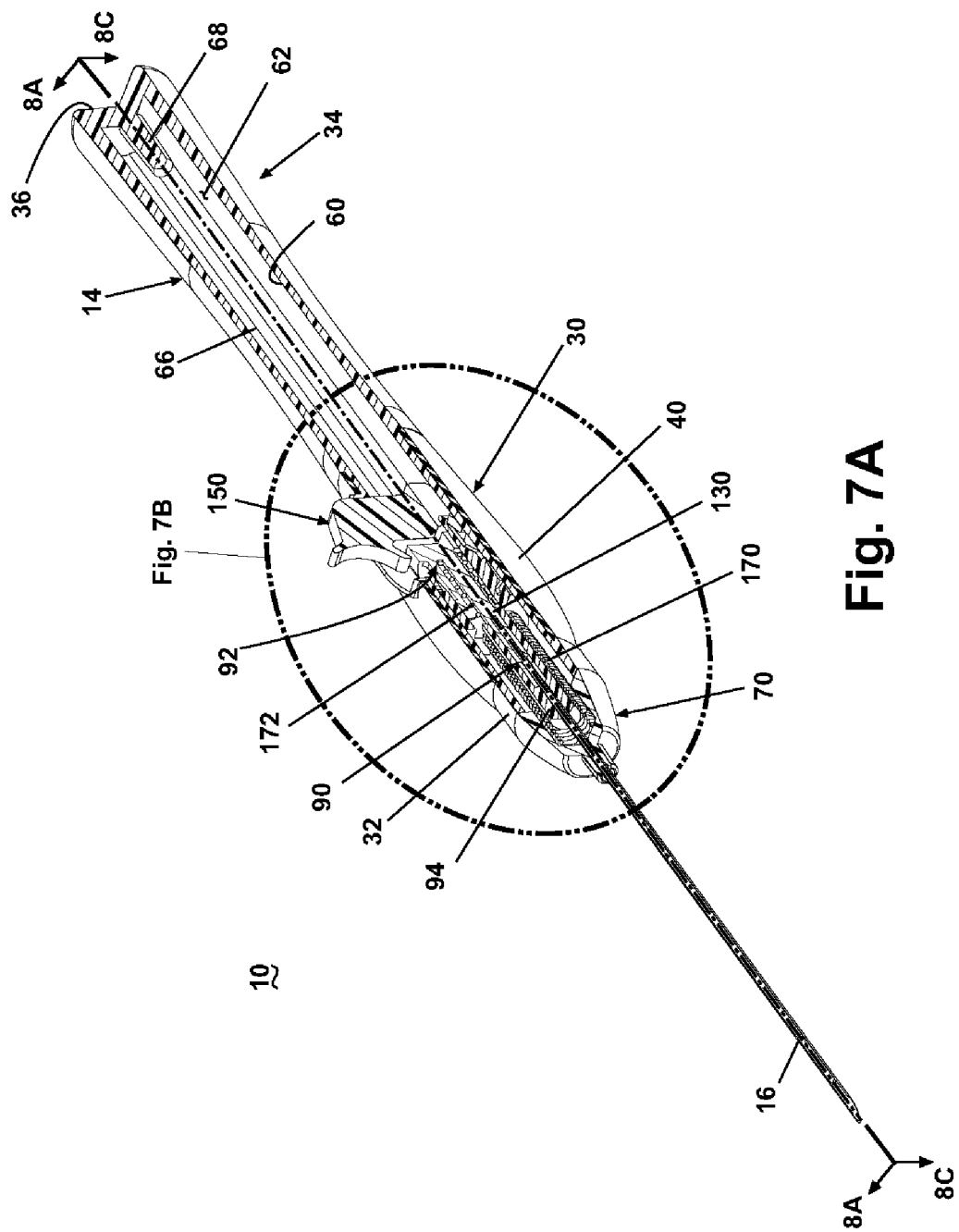

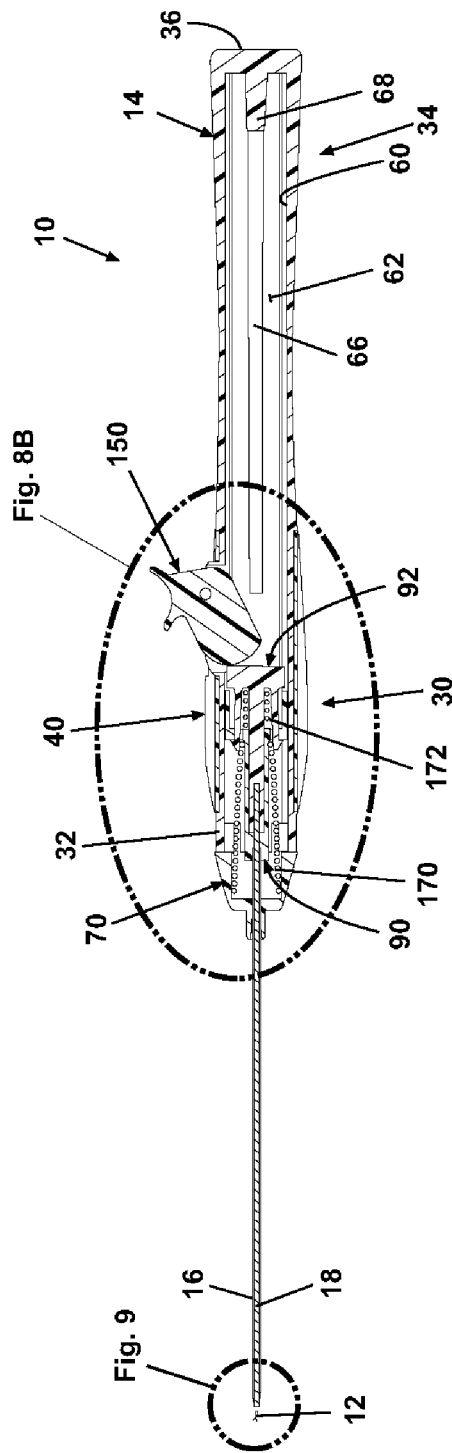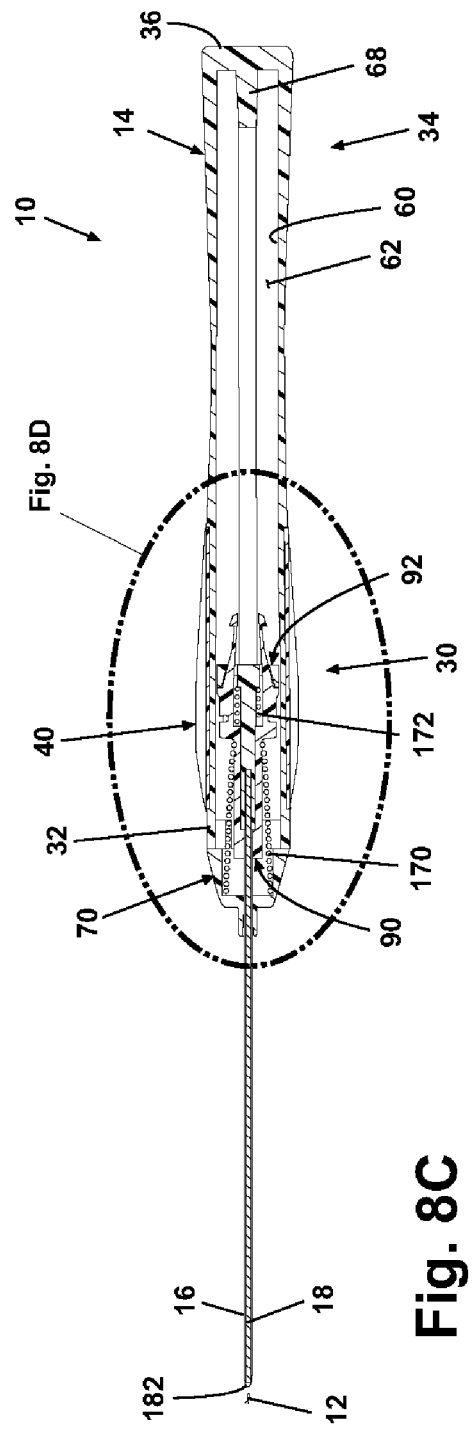

MARKING DEVICE WITH RETRACTABLE CANNULA

FIELD OF THE INVENTION

The invention relates generally to a device for implanting an imaging marker in a tissue mass and particularly to a marking device having a cannula that retracts into a handle following implantation of the imaging marker in the tissue mass.

DESCRIPTION OF THE RELATED ART

Subcutaneous imaging markers are commonly implanted in humans to identify a particular location in various areas and organs of the body. For example, markers are positioned at biopsy sites so that a practitioner can readily identify the tissue sample location after the biopsy procedure is completed. Markers are also used to denote the locations of lesions for therapeutic procedures, such as chemotherapy. Typically, markers located within the body can be viewed by various imaging techniques, such as radiography, ultrasound, and magnetic resonance imaging (MRI).

Various devices and methods have been developed for implanting a marker at a predetermined site in a tissue mass. One method of implanting a marker involves inserting a probe into the tissue mass and, with guidance from imaging systems, placing the tip of the probe near a predetermined location. Once the probe is in place and the biopsy is executed, a device comprising a flexible cannula, a stylet slidably mounted in the cannula, and the imaging marker positioned in the cannula distally of the stylet is manually threaded through the probe and positioned with the tip of the cannula at the predetermined location. Thereafter, the stylet is advanced distally to eject the imaging marker from the cannula at the predetermined location, and the cannula and the stylet are removed from the probe.

Other marking devices are self-contained in that they do not require a pre-inserted probe to guide the device to the predetermined location. Rather, such self-contained devices typically comprise a handle that supports a rigid cannula with a sharpened tip and a stylet mounted in the cannula. The imaging marker is positioned in the cannula distally of the stylet. In operation, the cannula is inserted into the body, and its sharpened, distal tip is placed at the predetermined location using imaging systems for guidance. The imaging marker can be implanted in one of two ways: the stylet advances distally to eject the marker from the cannula, or the cannula retracts relative to the stationary stylet to expose the marker to the predetermined location. Following implantation, the handle is pulled proximally to remove the cannula and the stylet from the body. The practitioner must be careful when pulling the marking device from the body because the sharpened tip of the cannula, which has been in contact with the patient's blood, is exposed and can potentially stab the practitioner, other persons assisting with the marking procedure, or even the patient if the practitioner accidentally moves the marking device towards the patient after removal of the marking device from the body. Thus, it is desirable for a self-contained marking device to comprise a cannula that retracts entirely into the handle following implantation of the imaging marker at the predetermined location.

SUMMARY OF THE INVENTION

A marking device according to one embodiment of the invention comprises a handle having a handle proximal end and a handle distal end and defining a hollow interior, a cannula having a cannula distal end and slidably mounted to the handle for slidable movement between an extended position where the cannula distal end extends beyond the handle distal end and a retracted position where the cannula distal end is received within the hollow interior, a stylet having a stylet distal end and slidably mounted to the handle for slidable movement between a ready position where the stylet distal end is proximal of the cannula distal end to form a marker recess in the cannula between the cannula distal end and the stylet distal end and an implant position where the stylet distal end extends into at least the marker recess, an imaging marker located within the marker recess, and an actuator operably coupled to the stylet and the cannula to effect movement of the stylet from the ready position to the implant position to eject the marker from the marker recess and movement of the cannula from the extended position to the retracted position.

The movement of the cannula from the extended position to the retracted position can occur after the movement of the stylet from the ready position to the implant position.

The stylet distal end can extend to at least the cannula distal end when in the implant position. The stylet distal end can extend beyond the cannula distal end when in the implant position.

The actuator can be configured to effect movement of the stylet from the implant position to a withdrawn position where the stylet is retracted into the hollow interior of the handle. The actuator can be configured to effect movement of the stylet from the implant position to the withdrawn position when effecting movement of the cannula from the extended position to the retracted position. The stylet distal end can be received within the hollow interior of the handle when in the withdrawn position.

The actuator can manually move the stylet from the ready position to the implant position. The actuator can automatically move the cannula from the extended position to the retracted position. The actuator can automatically effect movement of the stylet from the implant position to a withdrawn position where the stylet is retracted into the hollow interior of the handle when automatically moving the cannula from the extended position to the retracted position. The stylet distal end can be received within the hollow interior of the handle when in the withdrawn position.

The actuator can comprise a cannula biasing element operably coupled with the cannula in the handle to bias the cannula to the retracted position. The actuator can further comprise a trigger mounted to the handle and operable between a locked position where the trigger prevents movement of the cannula to the retracted position by the biasing element and a cannula release position where the trigger does not prevent movement of the cannula to the retracted position by the biasing element. The actuator can further comprise a cannula mount that supports a proximal end of the cannula for sliding movement in the hollow interior and operably couples the biasing element with the cannula. The actuator can further comprise a stylet mount that supports a proximal end of the stylet in the hollow interior. The actuator can further comprise a stylet biasing element operably coupled with the stylet mount in the hollow interior to bias the stylet to the ready position. The cannula mount can be operably coupled with the stylet mount so that the cannula mount directs the stylet mount proximally in the hollow interior to move the stylet to a withdrawn position where the stylet is retracted into the hollow interior when the cannula moves to the retracted position. The trigger can comprise a cam surface that rides along the stylet mount as the trigger moves from the locked position to the cannula release position to displace the stylet mount and move the stylet to the implant position. The cam surface can ride off the stylet mount as the trigger reaches the stylet advance position to the cannula release position to effect proximal movement of the stylet mount and the cannula mount.

The cannula distal end can comprise at least one imageable marking. The cannula can be rigid. The cannula can terminate at a sharpened tip at the cannula distal end. Alternatively, the cannula can be flexible.

A marking device according to another embodiment of the invention comprises a handle having a handle proximal end and a handle distal end and defining a hollow interior, a cannula having a cannula distal end and slidably mounted to the handle for slidable movement between an extended position where the cannula distal end extends beyond the handle distal end and a retracted position where the cannula distal end is received within the hollow interior, a stylet having a stylet distal end located in the cannula proximal of the cannula distal end to form a marker recess in the cannula between the cannula distal end and the stylet distal end, an imaging marker located within the marker recess, and an actuator operably coupled to the cannula to effect movement of the cannula from the extended position to the retracted position to expose the marker.

The stylet can be slidably mounted to the handle for slidable movement to a withdrawn position where the stylet is retracted into the hollow interior. The stylet distal end can be received within the hollow interior of the handle when in the withdrawn position. The stylet can be operably coupled to cannula so that the stylet moves to the withdrawn position when the cannula moves to the retracted position. Movement of the stylet to the withdrawn position can be delayed until the cannula distal end is at least at the stylet distal end to eliminate the marker recess.

The actuator can comprise a cannula biasing element operably coupled with the cannula in the handle to bias the cannula to the retracted position. The stylet can be operably coupled with the cannula so that movement of the cannula to the retracted position by the biasing element moves the stylet with the cannula to a withdrawn position where the stylet is retracted into the hollow interior.

The cannula distal end can comprise at least one imageable marking.

A method according to one embodiment of the invention of implanting an imaging marker into a tissue mass with a marking device comprising a handle defining a hollow interior, a cannula having a cannula distal end and slidably mounted to the handle, a stylet having a stylet distal end located in the cannula proximal of the cannula distal end to form a marker recess in the cannula between the cannula distal end and the stylet distal end, and an imaging marker located within the marker recess comprises implanting the imaging marker from the marker recess into the tissue mass, and retracting the cannula entirely into the handle.

The retracting of the cannula entirely into the handle can comprise retracting the cannula distal end into the hollow interior. The retracting of the cannula entirely into the handle can comprise automatically retracting the cannula entirely into the handle. The method can further comprise retracting the stylet with the cannula. The method can further comprise positioning the cannula distal end in the tissue mass with an imaging system.

The method can further comprise retracting the stylet into the handle. The retracting of the stylet into the handle can occur during the retracting of the cannula entirely into the handle. The retraction of the stylet can be delayed until the cannula distal end is retracted to at least at the stylet distal end to eliminate the marker recess. The implanting of the imaging marker can occur during the retracting of the cannula to expose the imaging marker to the tissue mass. Alternatively, the implanting of the imaging marker can comprise extending the stylet at least into the marker recess to expel the imaging marker from the marker recess. The extending of the stylet at least into the marker recess can comprise manually extending the stylet at least into the marker recess.

BRIEF DESCRIPTION OF THE DRAWINGS

In the drawings:

FIG. 4 is a perspective sectional view of a handle from the marking device of FIG. 1.

FIG. 7A is a sectional view taken along line 7-7 of FIG. 1 with the cannula in an extended position and the stylet in a ready position.

FIG. 8A is a sectional view taken along line 8A-8A of FIG. 7A, with the stylet moved to an implant position.

FIG. 8C is a sectional view taken along line 8C-8C of FIG. 7A, with the stylet moved to the implant position.

DESCRIPTION OF THE PREFERRED EMBODIMENT

Figure 1:
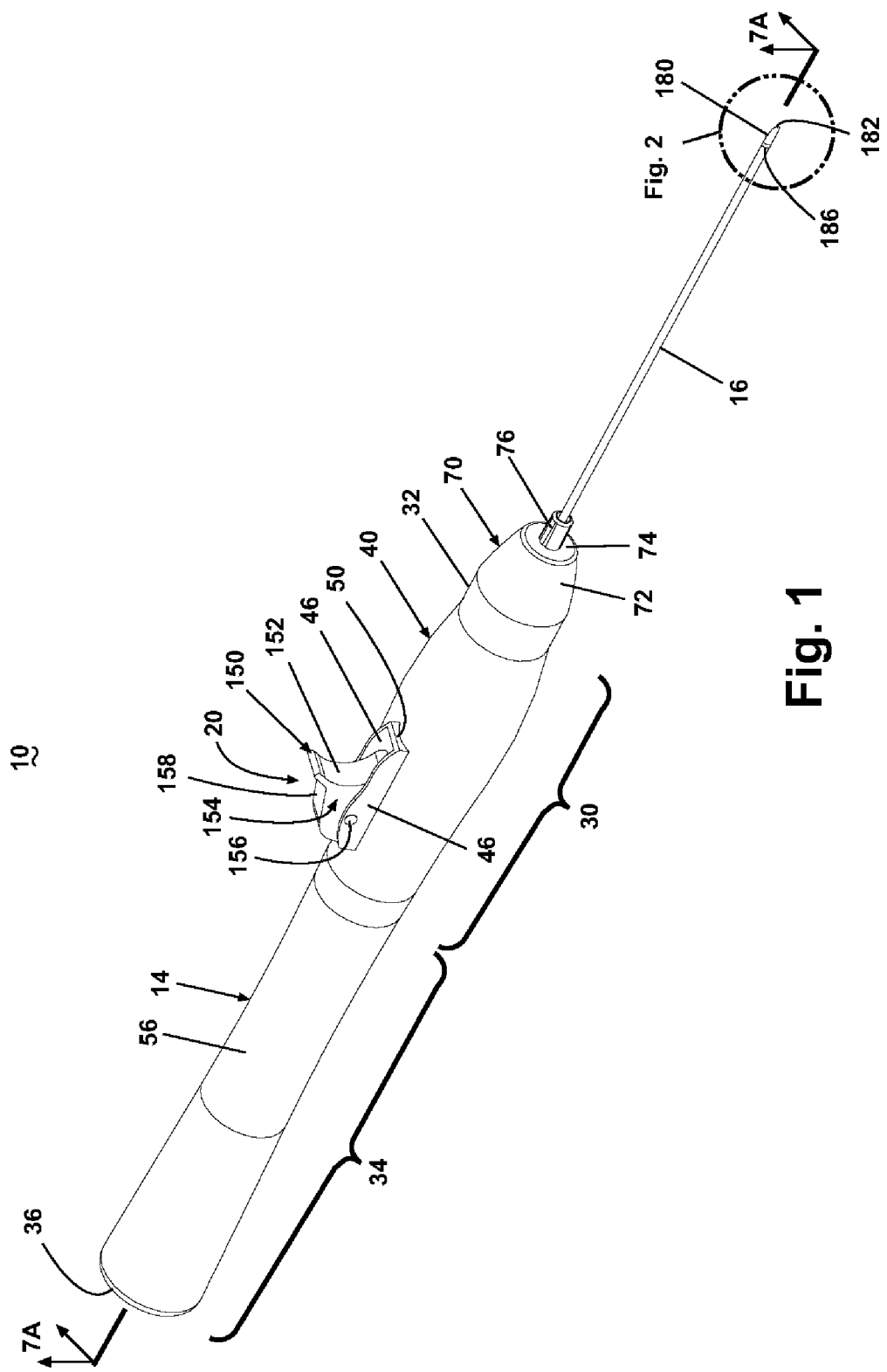
FIG. 1 is a perspective view of a marking device according to one embodiment of the invention.
Figure 2:
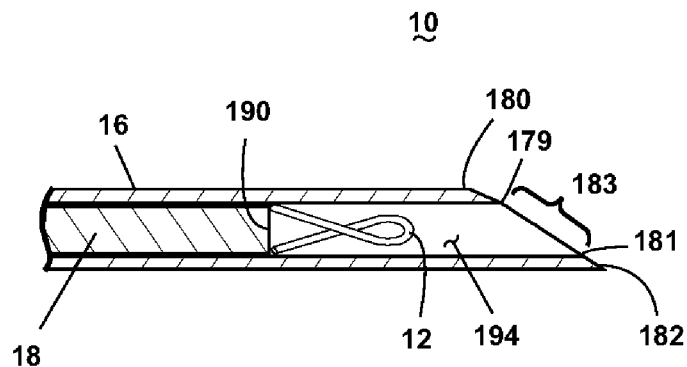
FIG. 2 is an enlarged sectional view of the area indicated in FIG. 1.
Figure 3:
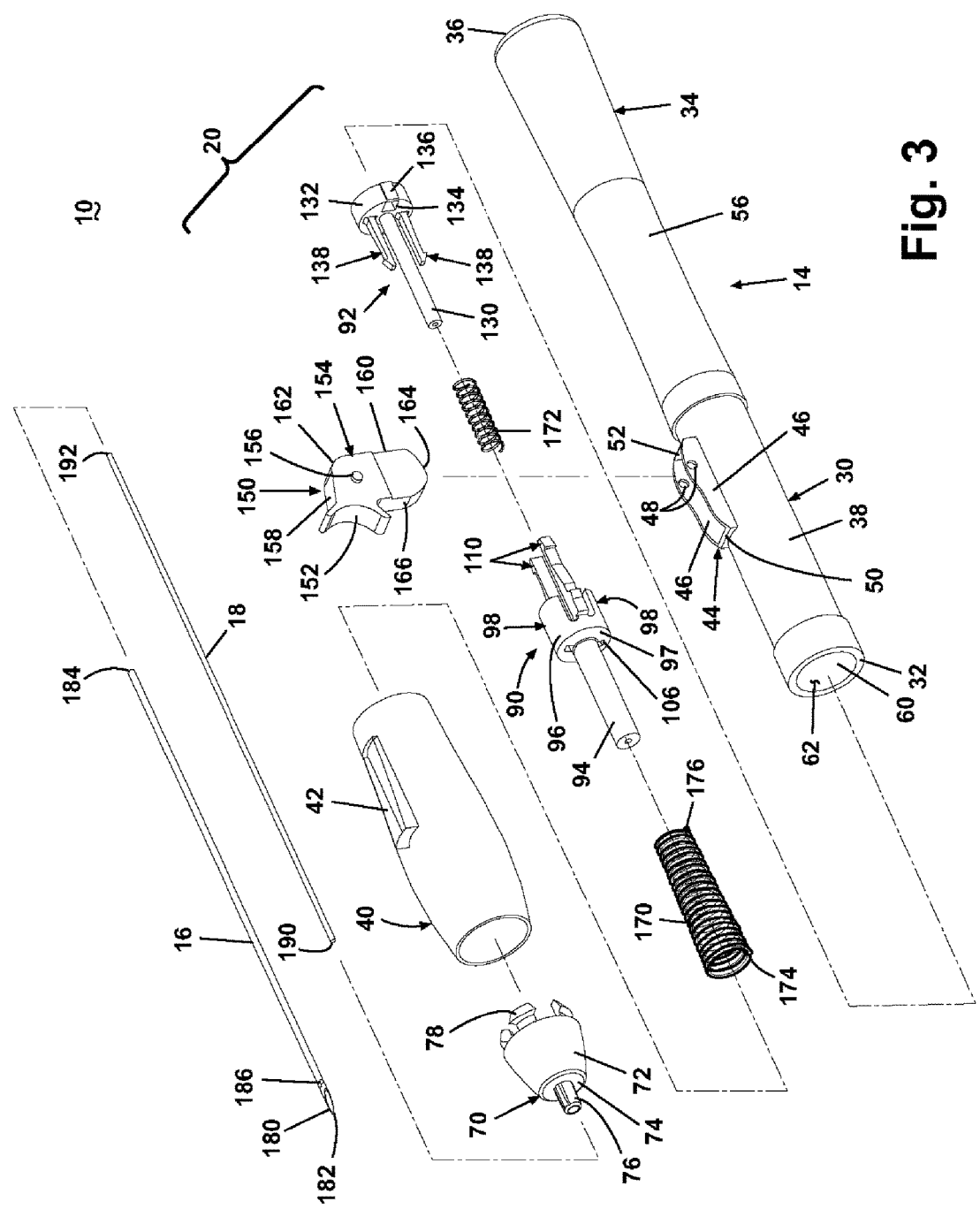
FIG. 3 is an exploded view of the marking device of FIG. 1.

Referring now to the figures, FIG. 1 illustrates a marking device 10 according to one embodiment of the invention for implanting an imaging marker 12, seen in FIG. 2, at a predetermined location in a tissue mass. Referring additionally to FIG. 3, the marking device 10 comprises a handle 14 that supports a cannula 16 slidably mounted thereto and a stylet 18 received within the cannula 16 and slidably mounted to the handle 14. An actuator 20 also mounted to the handle 14 effects movement of the stylet 18 and the cannula 16 to eject the imaging marker 12 from the marking device 10 and to retract the cannula 16 into the handle 14 following ejection of the imaging marker 12. The imaging marker 12 can be any suitable imaging marker made of any suitable non-bioabsorbable material, bioabsorbable material, or combinations thereof. Exemplary materials include, but are not limited to, metals, such as titanium and stainless steel, and polymers, such as polyvinyl alcohol (PVA), including combinations of such materials Examples of suitable imaging markers are disclosed in U.S. Pat. Nos. 6,356,782; 6,371,904; and 6,575,991, which are incorporated herein by reference in their entirety.

As best seen in FIGS. 3 and 4, the handle 14 comprises a distal section 30 that terminates in an open distal end 32 and an integral proximal section 34 that terminates at a closed proximal end 36. The distal section 30 includes a grip area 38 having a reduced outer diameter to accommodate a generally resilient grip 40 that surrounds the grip area 38 and has an aperture 42 to accommodate a trigger mount 44 located in the grip area 38 of the handle 14. The trigger mount 44 comprises a pair of spaced side walls 46, each having a pivot aperture 48, joined by a distal wall 50 and a proximal wall 52. The walls 46, 50, 52 surround a trigger opening 54 in the grip area 38 sized to receive and accommodate movement of the actuator 20, as will be described in more detail below. The proximal section 34 gradually tapers proximally from the grip area 38 and distally from the proximal end 36 to a hand rest area 56 contoured to support a palm portion of the user's hand.

Together, the distal section 30 and the proximal section 34 have an inner surface 60 that defines a generally cylindrical hollow interior 62. As best seen in FIG. 4, the inner surface 60 includes a stop 64 that extends radially into the hollow interior 62 from the grip area 38 near the trigger mount 44. Additionally, a pair of diametrically opposed guide grooves 66, one of which is visible in FIG. 4, is formed along the inner surface 60 from a proximal side of the trigger mount 44 to the proximal end 36. The handle 14 further includes a proximal stop 68 projecting into the hollow interior 62 from the proximal end 36.

Referring again to FIG. 3, the distal end 32 of the handle 14 is closed by a handle cap 70. The handle cap 70 comprises a generally hollow frustoconical body 72 with a distal endwall 74 from which extends a nose 76 sized to slidably receive the cannula 16. A plurality of resilient prongs 78 project proximally from the body 72 and mate with the distal end 32 of the handle 14 to mount the handle cap 70 to the handle 14. For convenience of this description, the handle cap 70 is described as being separate from the handle 14. However, the handle cap 70 can be considered as part of the handle 14 and can even be integrated with the handle 14.

Figure 5A:
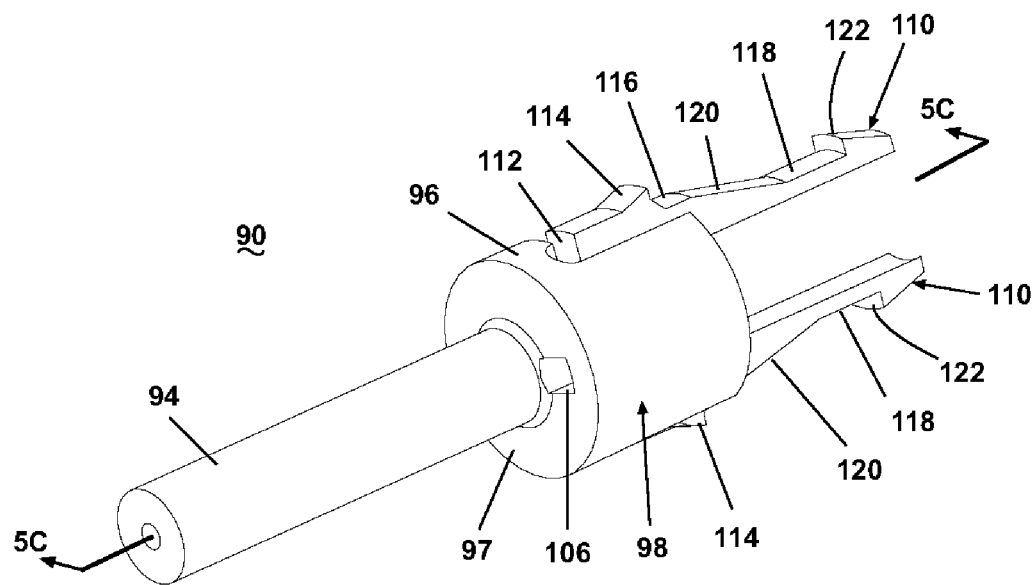
FIG. 5A is a front perspective view of a cannula mount for supporting a cannula of the marking device of FIG. 1.
Figure 5B:
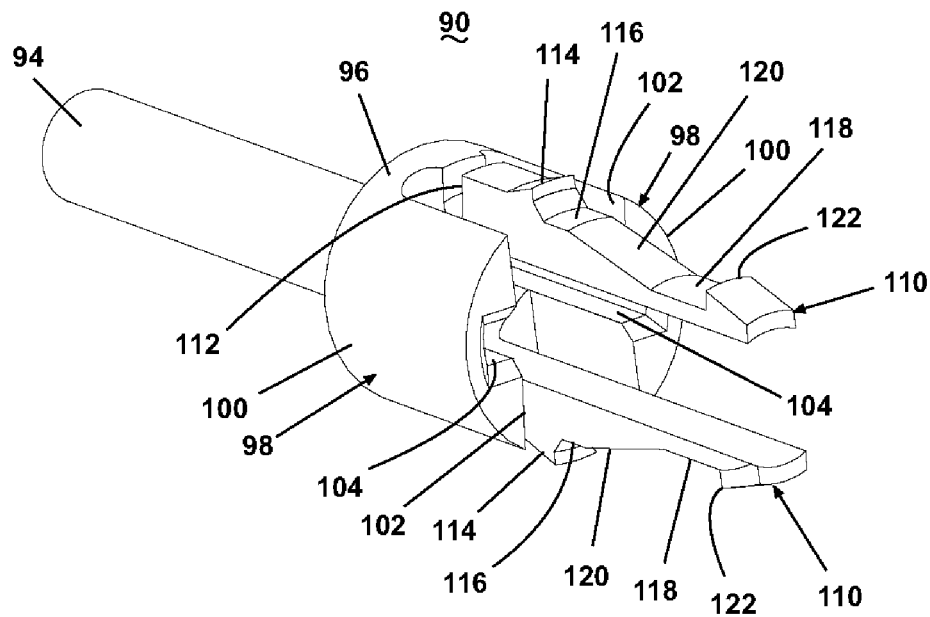
FIG. 5B is a rear perspective view of the cannula mount from FIG. 5A.
Figure 5C:
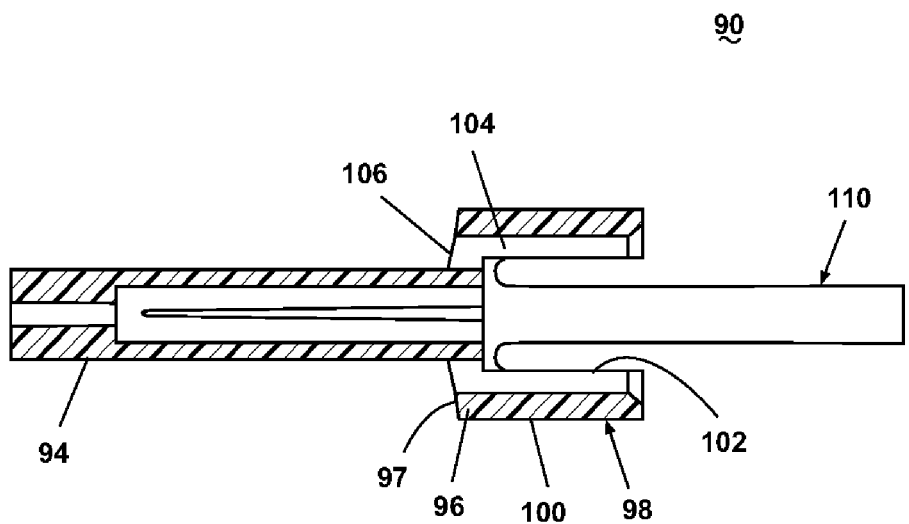
FIG. 5C is a sectional view of the cannula mount taken along line 5C-5C of FIG. 5A.

The actuator 20 comprises a cannula mount 90 and a stylet mount 92 that slidably support the cannula 16 and the stylet 18, respectively, in the handle 14. As shown in FIGS. 5A-5C, the cannula mount 90 includes an elongated cannula support shaft 94 integral with a generally orthogonal annular body 96 having an annular distal face 97. A pair of opposed legs 98 having an arcuate outer surface 100 and a generally straight inner surface 102 extend proximally from the annular body 96, and each of the legs 98 has a channel 104 formed therein that terminates at a corresponding opening 106 formed through the annular body 96. The channels 104 are formed in the inner surface 102 so that the channels 104 face one another. The cannula mount 90 further comprises a pair of diametrically opposed resilient prongs 110 positioned between the legs 98. The resiliency of each prong 110 is enhanced by a U-shaped notch 112 at the juncture between the prong 110 and the annular body 96. Each prong 110 comprises a raised stop 114 disposed distally of a distal flat surface 116 joined to a proximal flat surface 118 by an inclined surface 120, and each prong 110 terminates at an outwardly projecting tang 122 adjacent the proximal flat surface 118.

Figure 6A:
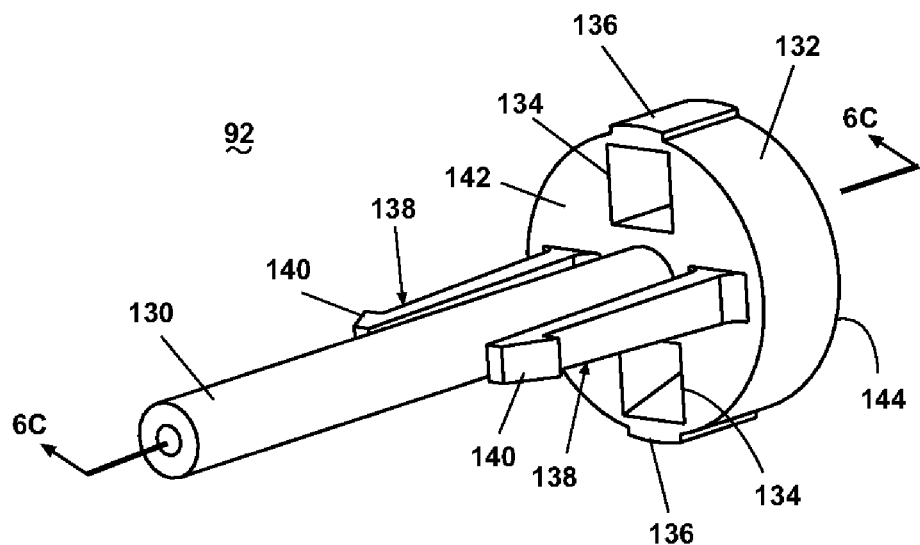
FIG. 6A is a front perspective view of a stylet mount for supporting a stylet of the marking device of FIG. 1.
Figure 6B:
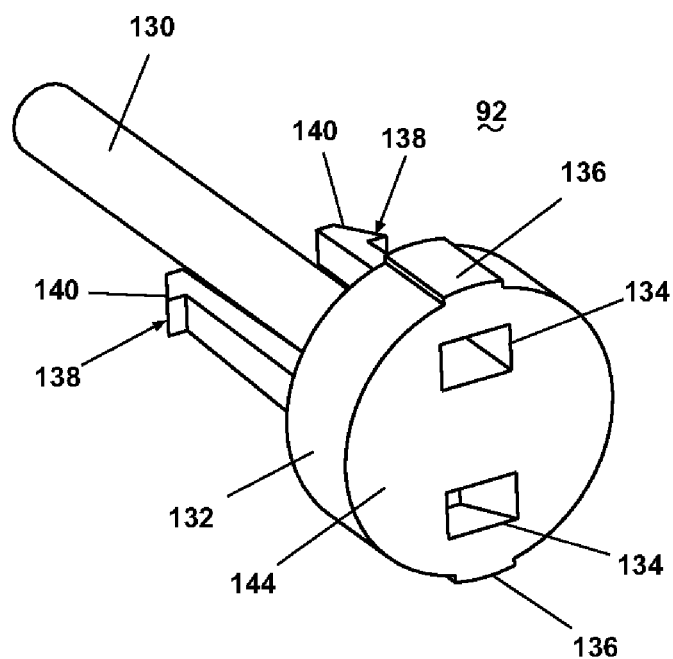
FIG. 6B is a rear perspective view of the stylet mount from FIG. 6A.
Figure 6C:
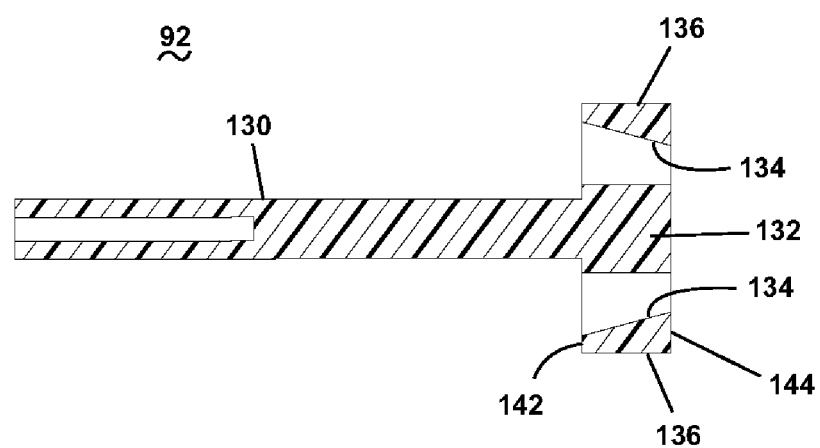
FIG. 6C is a sectional view of the stylet mount taken along line 6C-6C of FIG. 6A.

The stylet mount 92, as shown in FIGS. 6A-6C, comprises an elongated stylet support shaft 130 integral with a generally orthogonal cylindrical body 132. The body 132 has a pair of diametrically opposed prong apertures 134 formed therein from a distal face 142 to a proximal face 144 of the body 132 and sized to receive the prongs 110 of the cannula mount 90. As best viewed in FIG. 6C, the prong apertures taper from the distal face 142 to the proximal face 144. The body 132 further includes a pair of guide projections 136 extending radially from the body 132 in radial alignment with the prong apertures 134. A pair of diametrically opposed prongs 138 extends distally from the body 132, and each prong 138 terminates in an outwardly projecting tang 140. The prongs 138 are oriented along a diameter generally orthogonal to a diameter that contains the prong apertures 134 with the stylet support shaft 130 between the prongs 138.

Referring back to FIG. 3, the actuator 20 further comprises a trigger 150 rotatably mounted to the trigger mount 44 of the handle 14. Although the trigger 150 can move relative to the handle 14, it will be described with respect to the orientation shown in FIG. 3. The trigger 150 includes a distally facing arcuate finger rest 152 and an irregularly shaped body 154 having a pivot member 156 on each side thereof. The body 154 is bounded by a sloped upper surface 158 extending proximally of the finger rest 152 and joined to a generally straight proximal surface 160 by a fillet 162. The rest of the body 154 is defined by a curved cam surface having a distal cam surface 166 and a lower cam surface 164. The distal cam surface 166 extends from the finger rest 152 to the lower cam surface 164, which terminates at the straight proximal surface 160.

In addition to the cannula mount 90, the stylet mount 92, and the trigger 150, the actuator 20 comprises a pair of biasing members: a cannula mount biasing member 170 and a stylet mount biasing member 172. According to the illustrated embodiment of the invention, the biasing members 170, 172 are compression springs. Preferably, the cannula mount biasing member 170 tapers from a distal end 174 to a proximal end 176.

The cannula 16 is generally hollow and comprises a distal end 180 defining a tip 182 and a proximal end 184 mounted to the cannula support shaft 94 of the cannula mount 92. The cannula 16 is preferably sufficiently rigid to permit the direct insertion of the cannula 16 into a tissue mass. Alternatively, the cannula 16 can be flexible for use with a probe or the like. The tip 182 is preferably pointed for insertion through skin and into the tissue mass; however, the tip 182 can optionally be blunt, for example, if the marking apparatus 10 is utilized with a probe or the like. Further, the distal end 180 of the cannula 16 can be beveled, as best seen in FIG. 2, from a bevel proximal edge 179 to a bevel distal edge 181 to define a bevel opening 183. Preferably, the cannula 16 is a 17-gage (0.058 inch outer diameter) cannula, with an inner diameter ranging from 0.049 to 0.051 inches. Furthermore, the distal end 180 of the cannula 16 can be designed for enhanced visibility using common imaging techniques, such as radiography, ultrasonography, and magnetic resonance imaging (MRI). For example, the distal end 180 can include imageable markings 186, as seen in FIG. 3. With continued reference to FIG. 3 and additional reference to FIG. 2, the cannula 16 slidingly receives the stylet 18, which comprises a distal end 190 located in the cannula 16 and a proximal end 192 mounted to the stylet support shaft 130 of the stylet mount 92. Prior to use of the marking device 10, the distal end 190 of the stylet 16 is spaced inwardly from the tip 182 to form a marker recess 194, as best viewed in FIG. 2, for housing the imaging marker 12.

When the marking device 10 is in an assembled condition, as shown in FIG. 7A, the stylet mount 92 is mounted in the hollow interior 62 with the guide projections 136 positioned in general alignment with the guide grooves 66. The stylet 18 extends from the stylet support shaft 130, through the cannula support shaft 94 of the cannula mount 90, which is located distally of the stylet mount 92 in the hollow interior 62, and out the distal end 32 of the handle 14 through the nose 76 of the handle cap 70. The cannula mount 90 is positioned so that the cannula 16 also leaves the distal end 32 of the handle 14 through the nose 76 of the handle cap 70. The relative positioning of the cannula mount 90 and the stylet mount 92 in the hollow interior 62 is such that the distal end 190 of the stylet 18 is spaced from the tip 182 to form the marker recess 194 (FIG. 2). In this condition, the cannula 16 is in an extended position where it extends from the distal end 32 of the handle 14, and the stylet 18 is in a ready position in the extended cannula 16.

Figure 7B:
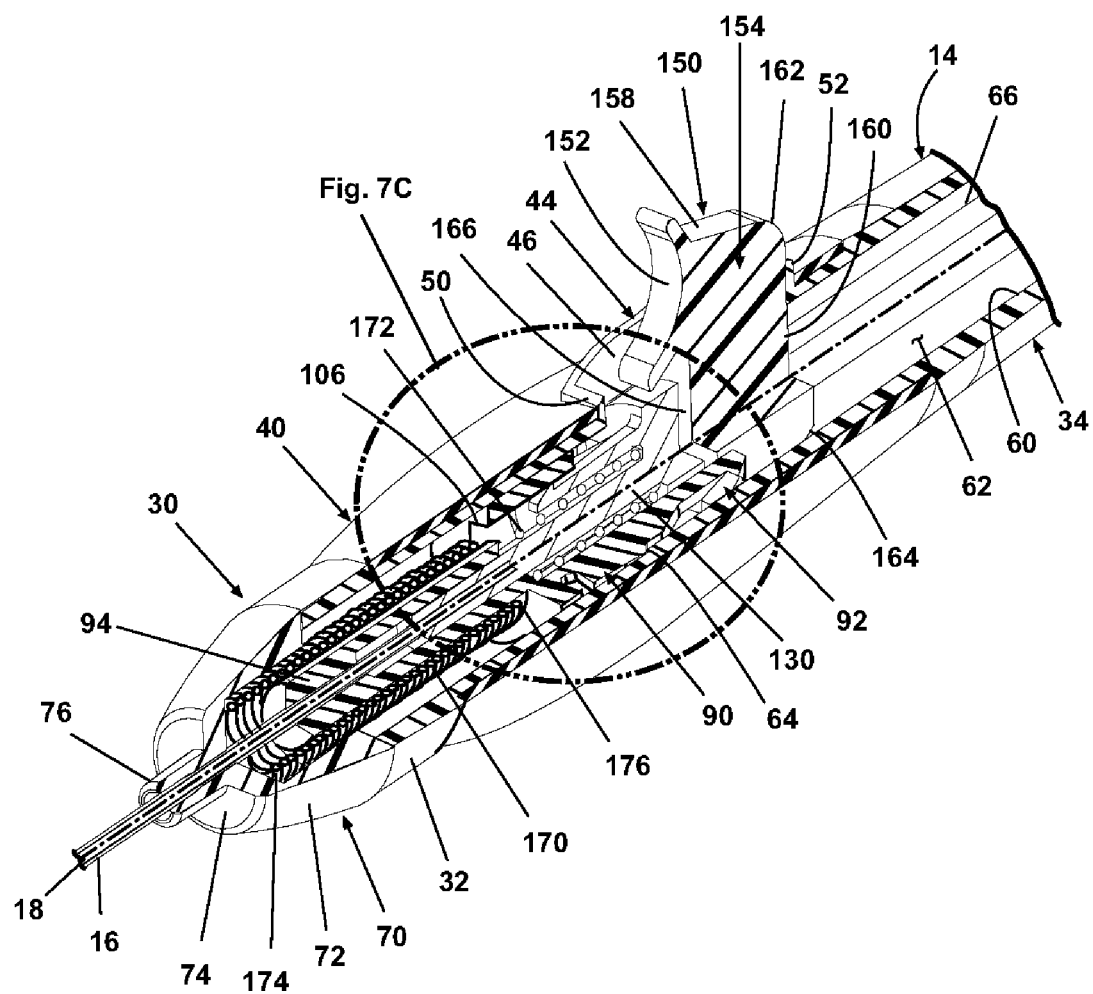
FIG. 7B is an enlarged view of the area indicated in FIG. 7A.
Figure 7C:
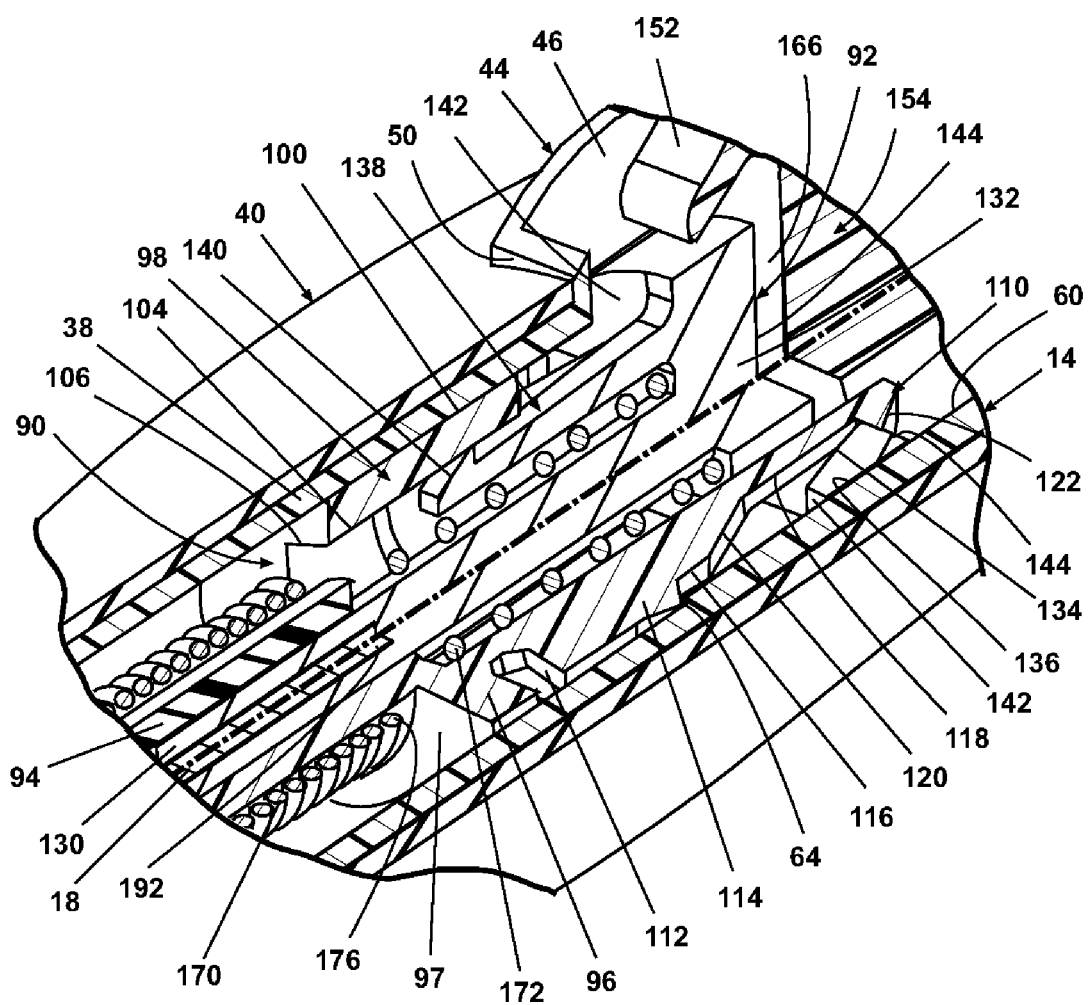
FIG. 7C is an enlarged view of the area indicated in FIG. 7B.

As best seen in FIGS. 7B and 7C, the cannula mount 90 and the stylet mount 92 are axially aligned in the hollow interior 62 with the stylet mount prongs 138 partially inserted into the channels 104 of the cannula mount 90 and the stylet support shaft 130 partially received in the cannula support shaft 94 of the cannula mount 90. Additionally, the cannula mount prongs 110 extend through the prong apertures 134 of the stylet mount 92 with the tangs 122 abutting the proximal face 144 of the body 132 and the proximal flat surfaces 118 positioned in the prong apertures 134. The cannula mount prongs 110 naturally spread apart from one another to facilitate securing the cannula mount 90 to the stylet mount 92 in the position best seen in FIGS. 7B and 7C. Additionally, as a result of the natural resiliency of the cannula mount prongs 110, the stops 114 extend radially outward and abut the stop 64 of the handle 14 to help prevent proximal movement of the cannula mount 90 even though the cannula mount 90 is biased away from the handle cap 70 by the cannula mount biasing member 170, which abuts the handle cap 70 at the distal end 174 and the annular body 96 at the proximal end 176. Similarly, the stylet mount 92 is biased away from the cannula mount 90 by the stylet mount biasing member 172, which extends between the annular body 96 and the body 132 of the stylet mount 92. The interaction between the cannula mount prongs 110 and the stylet mount body 132 prevents retraction of the stylet mount 92 beyond the position shown in FIGS. 7B and 7C. Additionally, proximal movement of the stylet mount 92 and the cannula mount 90 is prevented in part by the trigger 150. The pivot mounts 156 are rotatably received by the pivot apertures 48 to mount the trigger 150 in the trigger mount 44 of the handle 14. The trigger 150 extends through the trigger opening 54 in a locked condition, shown in FIGS. 7B and 7C, where the proximal surface 160 abuts the proximal wall 52 of the trigger mount 44 to prevent counterclockwise rotation, relative to the orientation of FIGS. 7B and 7C, of the trigger 150, and the distal cam surface 166 faces the stylet mount 92.

Figure 9:
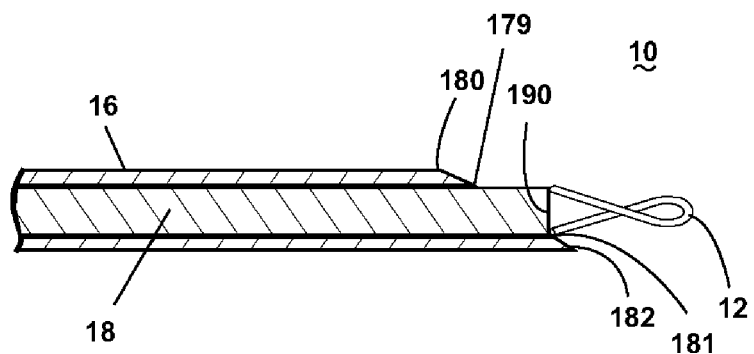
FIG. 9 is an enlarged sectional view of the area indicated in FIG. 8.
Figure 8B:
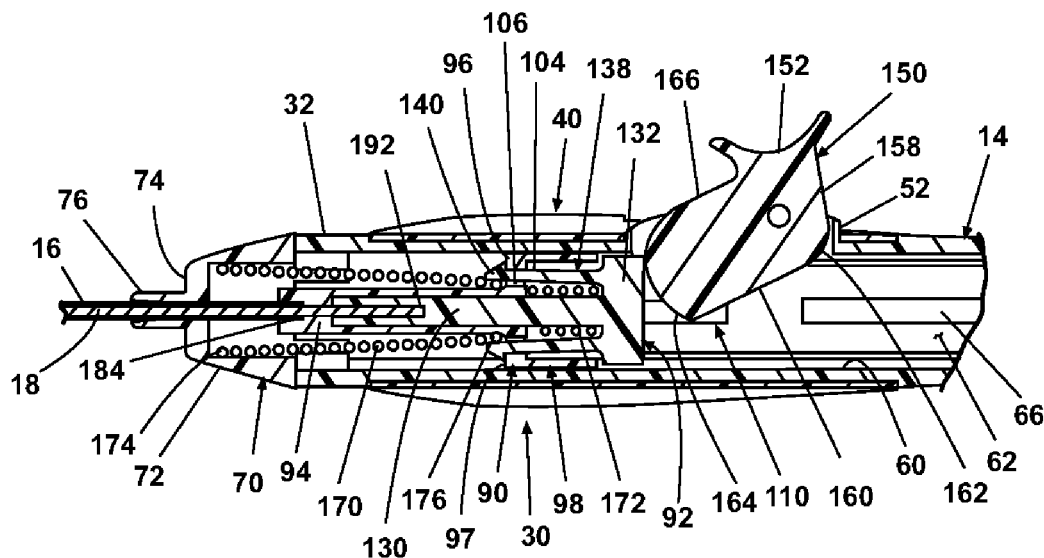
FIG. 8B is an enlarged view of the area indicated in FIG. 8A.
Figure 8D:
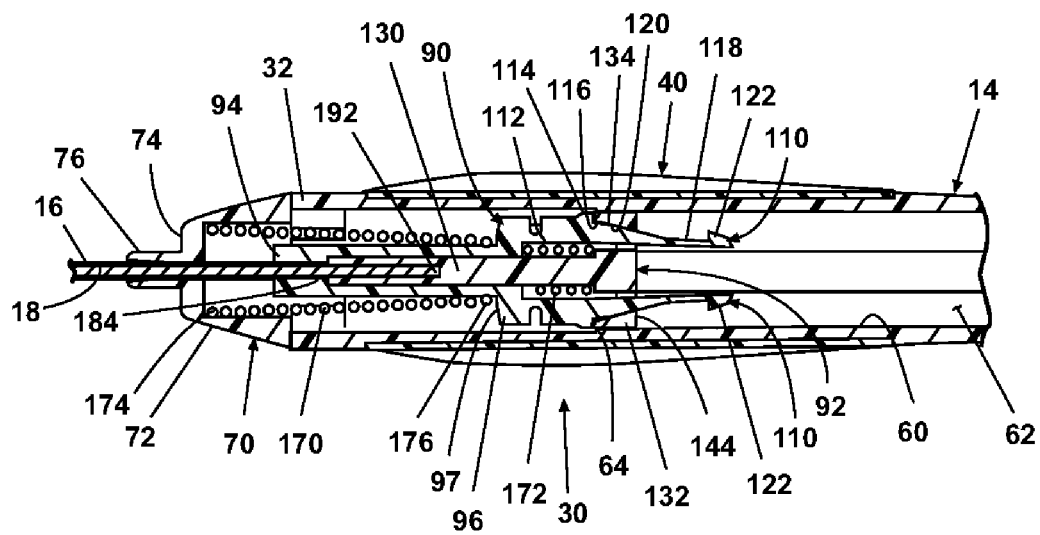
FIG. 8D is an enlarged view of the area indicated in FIG. 8C.

The trigger 150 is movable from the locked position shown in FIGS. 7A-7C to a stylet advance position shown in FIGS. 8A and 8C to displace the stylet 18 proximally and eject the imaging marker 12 from the marker recess 194, as shown in FIG. 9. Rotation of the trigger 150 clockwise, relative to the orientation of FIG. 8A, such as by rotation of the finger rest 152 by the user, causes the cam surface formed by the distal cam surface 166 and the lower cam surface 164 to abut the body 132 of the stylet mount 92 and ride along the proximal face 144 of the body 132 between the cannula mount prongs 110 while pushing the stylet mount 92 distally toward the cannula mount 90 against the bias of the stylet mount biasing member 172, as best seen in FIG. 8B. As a result, the tangs 140 of the stylet mount prongs 138 slide along the channels 104 of the cannula mount 90 until the tangs 140 slide through the openings 106 in the annular body 96 and flex outward to abut the distal face 97 of the annular body 96 and thereby secure the stylet mount 92 to the cannula mount 90 together in the position shown in FIG. 8B. At the same time, the body 132 rides distally along the cannula mount prongs 110, particularly along the inclined surfaces 120, as best seen in FIG. 8D. As the body 132 moves along the prongs 110, the taper of the prong apertures 134 forces the prongs 110 to flex toward each other at their respective notches 112 so that the stops 114 are no longer in abutting contact with the stop 64 on the interior surface 60 of the handle 14. Distal movement of the stylet mount 92 ceases when the body 132 reaches the distal flat surfaces 116. In this position, the trigger 150 prevents proximal movement of the cannula mount 90 and the stylet mount 92 by the cannula mount biasing member 170. Because the stylet mount 92 moves distally while the cannula mount 90 remains stationary, the stylet 16 advances distally into the marker recess 194 to an implant position to eject the imaging marker 12 therefrom, as shown in FIG. 9. Preferably, the stylet 18 is sized so that when the stylet 18 is in the implant position, the distal end 190 of the stylet 18 extends to at least the bevel proximal edge 179 at the bevel opening 183 to ensure that the imaging marker 12 reaches the bevel opening 183 for ejection from the marker recess 194. The stylet distal end 190 can also extend to a position between the bevel proximal edge 179 and the bevel distal edge 181 (i.e., a center point of the bevel and the bevel opening 183). Further, the stylet distal end 190 can extend to near the tip 182 of the cannula 16 (i.e., the bevel distal edge 181) or beyond the tip 182 to ensure complete ejection of the imaging marker 12 from the marker recess 194.

Figure 10A:
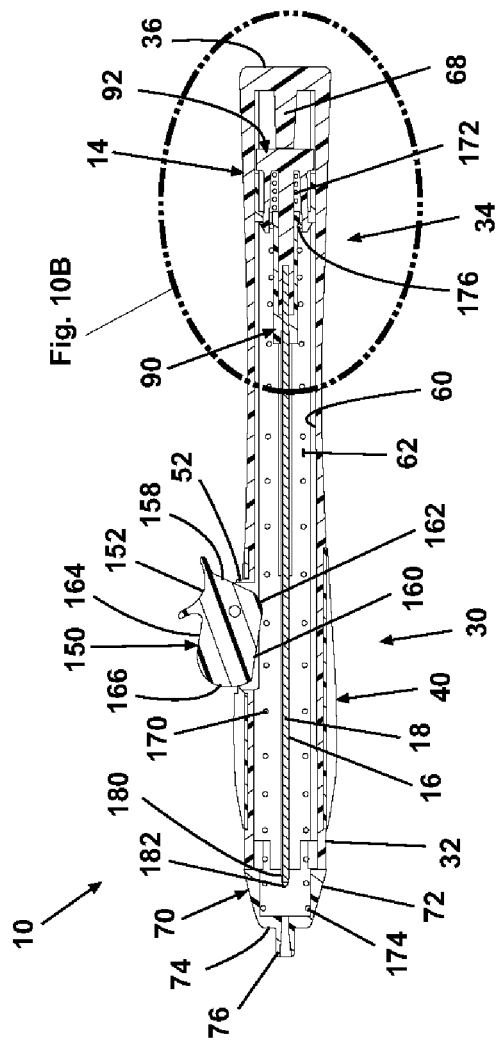
FIG. 10A is a sectional view similar to FIG. 8A with the cannula in a retracted position and the stylet in a withdrawn position.
Figure 10C:
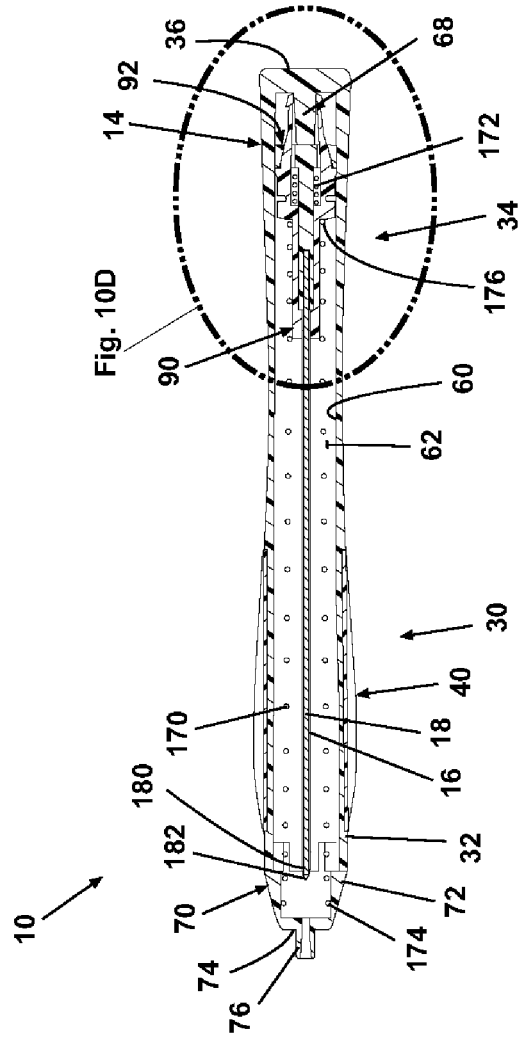
FIG. 10C is a sectional view similar to FIG. 8C with the cannula in the retracted position and the stylet in the withdrawn position.
Figure 10B:
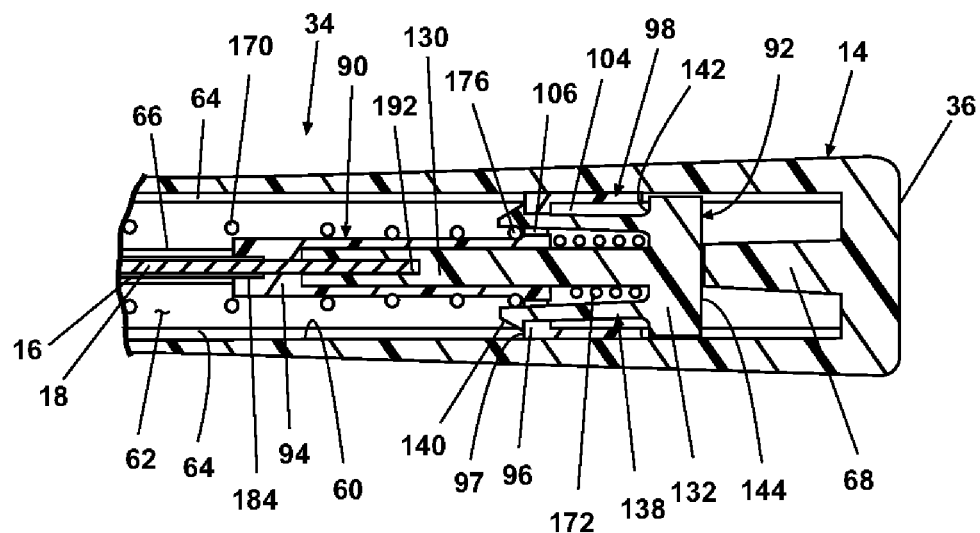
FIG. 10B is an enlarged view of the area indicated in FIG. 10A.
Figure 10D:
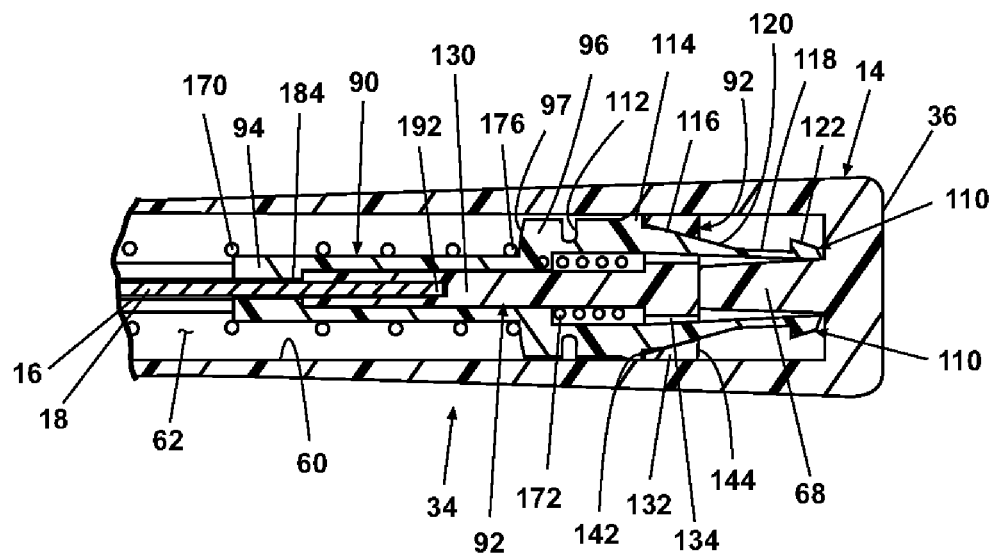
FIG. 10D is an enlarged view of the area indicated in FIG. 10C.

Continuing rotation of the trigger 150 beyond the stylet advance position to a cannula release position shown in FIGS. 10A and 10C retracts the cannula 16 and the stylet 18 into the hollow interior 62. While the trigger 150 rotates to the cannula release position, the cam surface formed by the distal cam surface 166 and the lower cam surface 164 rides off of the proximal face 144 of the stylet mount body 132 so that the trigger 150 no longer prevents proximal movement of the stylet mount 92 and the cannula mount 90 in the handle 14. With the trigger 150 no longer an obstacle and the stops 114 on the cannula mount prongs 110 no longer abutting the stop 64, the cannula mount biasing member 170 forces the cannula mount 90 and thereby the stylet mount 92, which is fixed to the cannula mount 90 by the stylet mount prongs 138 and the cannula mount prongs 110, proximally within the hollow interior 62 toward the proximal end 36 of the handle 14. Movement of the cannula mount 90 and the stylet mount 92 ceases when the stylet mount 92 abuts the proximal stop 68 with the prongs 110 on the cannula mount 90 straddling the stop 68, as best viewed in FIGS. 10B and 10D. During this movement, the guide projections 136 enter the guide grooves 66 formed in the interior surface 60 of the handle 14 to prevent rotation of the stylet mount 92 and thereby the cannula mount 90. Proximal movement of the cannula mount 90 and the stylet mount 92 retracts the cannula 16 and the stylet 18 into the hollow interior 62 to a retracted position and a withdrawn position, respectively. Preferably, when the cannula 16 is in the retracted position, the entire cannula 16, including the tip 182, is received within the handle 14 as seen in FIGS. 10A and 10C. Similarly, the entire stylet 18 is preferably received within the handle 14 when in the withdrawn position, but it within the scope of the invention for the distal end 190 to project from the nose 76 when the stylet 18 is in the withdrawn position.

Figure 11:
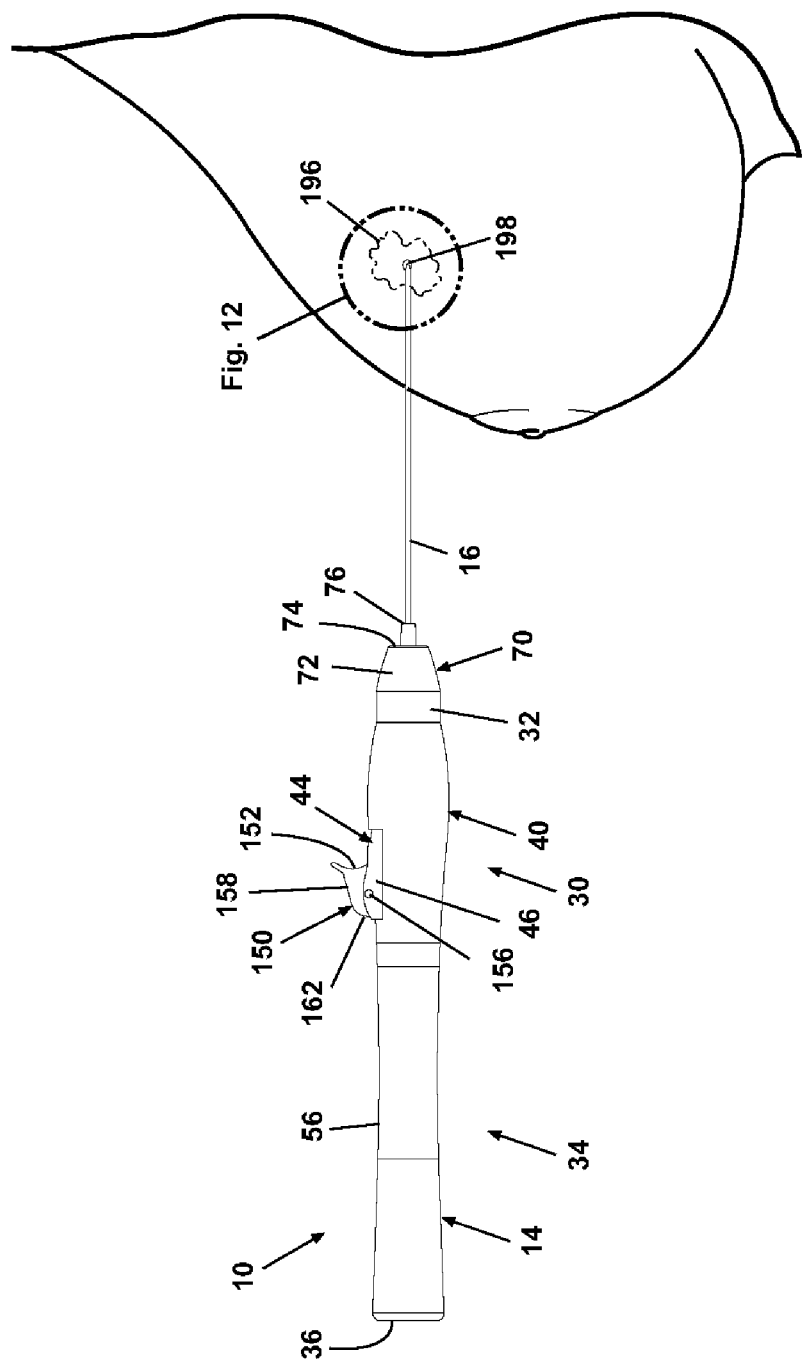
FIG. 11 is a side view of the marking device of FIG. 1 inserted into a tissue mass.
Figure 12:
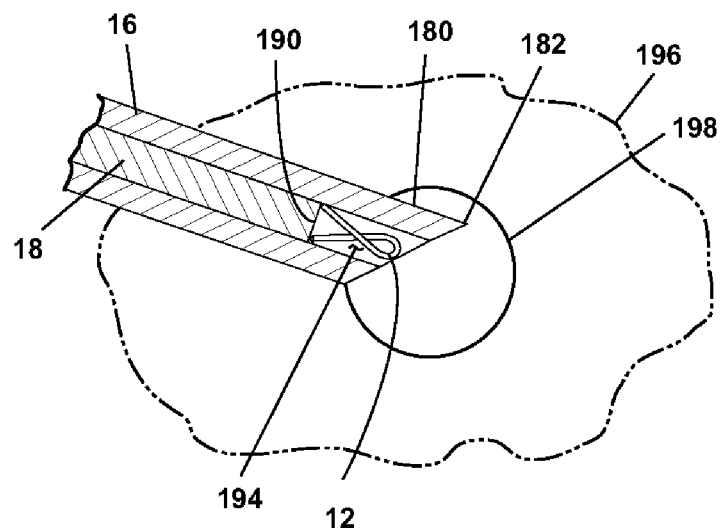
FIG. 12 is an enlarged view of the area indicated in FIG. 11 showing a distal end of the marking device positioned at a predetermined location in the tissue mass.
Figure 13:
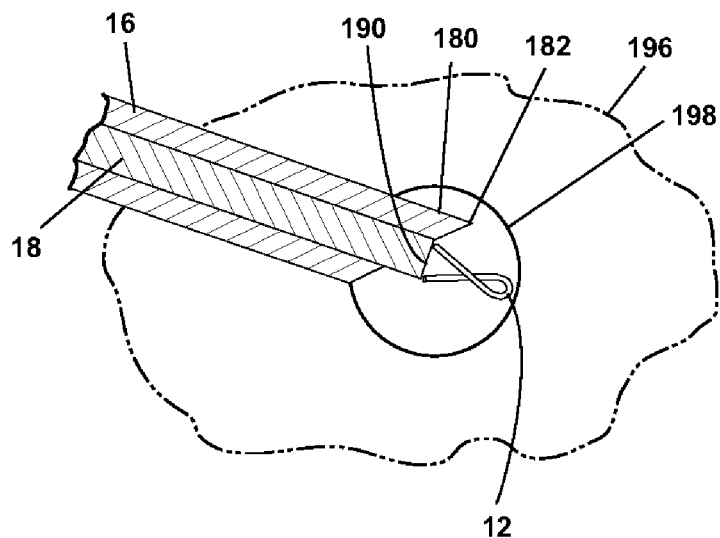
FIG. 13 is an enlarged view similar to FIG. 12 with an imaging marker expelled from the marking device at the predetermined location.

In operation, a practitioner grasps the marking device 10 at the hand rest area 56 and inserts the cannula tip 182 through the skin of patient's body into a tissue mass 196. An exemplary tissue mass 196 is a breast, as shown in FIG. 11. The practitioner places the tip 182 typically under the guidance of aforementioned imaging systems at or near a predetermined site 198, such as a biopsy site, as shown in FIG. 12. Once the cannula tip 182 is at the predetermined site 198, the practitioner places an index finger on the finger rest 152 of the trigger 150 and rotates the trigger 150 to move the trigger 150 from the locked position of FIGS. 7A-7C to the stylet advance position of FIGS. 8A-8D to move the stylet 18 from the ready position of FIGS. 7A-7C to the implant position of FIGS. 8A-8D and eject the imaging marker 12 from the marker recess 194 at the predetermined site 198, as illustrated in FIG. 13. The practitioner continues to the rotate the trigger 150 to the cannula release position of FIGS. 10A and 10B to simultaneously move the cannula 16 from the extended position of FIGS. 7A-7C and 8A-8D to the retracted position of FIGS. 10A-10D and the stylet 18 from the implant position of FIGS. 8A-8D to the withdrawn position of FIGS. 10A-10D to remove the cannula 16 and the stylet 18 from the tissue mass 196 as they retract into the handle 14. Preferably, rotation of the trigger 150 between the locked, stylet advance, and cannula release positions is substantially continuous such that the practitioner can implant the imaging marker 12 and retract the cannula 16 into the handle 14 in effectively a single operational step. With the cannula 16 retracted into the handle 14, the practitioner cannot accidentally stab himself or herself, others assisting with the procedure, or the patient with the marking device 10 following implantation of the imaging marker 12.

Figure 14:
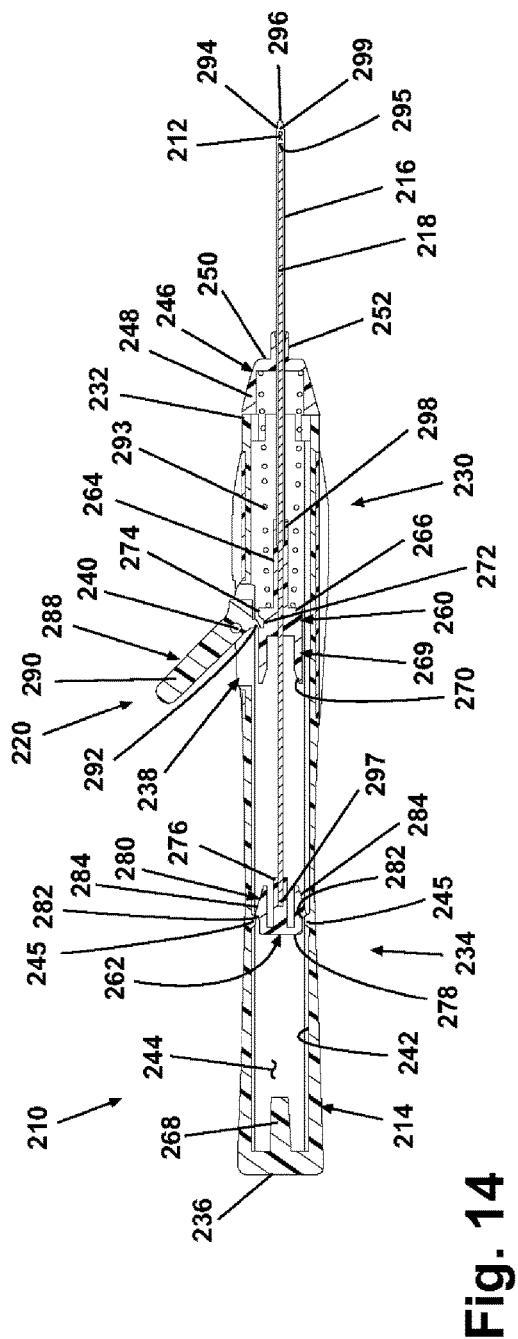
FIG. 14 is a sectional view of a marking device according to another embodiment of the invention, with a handle that supports a cannula in an extended position and a stylet in a ready position.

A marking device 210 according to another embodiment of the invention for implanting an imaging marker 212 at a predetermined location in a tissue mass is illustrated in FIGS. 14-17. Referring particularly to FIG. 14, the marking device 210 comprises a handle 214 that supports a cannula 216 slidably mounted thereto and a stylet 218 received within the cannula 216 and slidably mounted to the handle 214. An actuator 220 also mounted to the handle 214 effects proximal movement of the cannula 216 to expose the imaging marker 212 and to retract the cannula 216 and the stylet 218 into the handle 214 after exposing the imaging marker 212.

The handle 214 of the marking device 210 is similar to the handle 14 of the first embodiment marking device 10 and comprises a distal section 230 that terminates in an open distal end 232 and an integral proximal section 234 that terminates at a closed proximal end 236. A trigger mount 238 in the distal section 230 comprises a pivot mount 240 for mounting a portion of the actuator 220, as will be described in more detail below. Together, the distal section 230 and the proximal section 234 have an inner surface 242 that defines a generally cylindrical hollow interior 244. The handle 214 comprises a pair of stops 245 extending radially inward from the inner surface 242 in the hollow interior 244. The handle 214 further includes a proximal stop 268 projecting into the hollow interior 244 from the proximal end 236. The hollow interior 244 is closed at the distal end 232 of the handle 214 by a handle cap 246. The handle cap 246 comprises a generally hollow frustoconical body 248 with a distal end-wall 250 from which extends a nose 252 sized to slidably receive the cannula 216. For convenience of this description, the handle cap 246 is described as being separate from the handle 214. However, the handle cap 246 can be considered as part of the handle 214 and can even be integrated with the handle 214.

The actuator 220 comprises a cannula mount 260 and a stylet mount 262 that slidably support the cannula 216 and the stylet 218, respectively, in the handle 214. The cannula mount 260 includes an elongated cannula support shaft 264 integral with a generally orthogonal annular body 266 with a peripheral wall 274 having a trigger detent 272 formed therein. A pair of legs 269 having a sloped terminal cam surface 270 extends proximally from the annular body 266. The stylet mount 262 comprises an elongated stylet support shaft 276 integral with a generally orthogonal body 278 having a pair of diametrically opposed resilient arms 280 extending distally from the body 278 on opposite sides of the stylet support shaft 276. Each arm 280 comprises a proximal sloped stop surface 282 near the body 278 and terminates at an inclined cam follower surface 284.

With continued reference to FIG. 14, the actuator 220 further comprises a trigger 288 pivotally mounted to the trigger mount 238 of the handle 214. The trigger 288 includes a proximal finger rest 290 and a downwardly extending projection 292 integral with the finger rest 290. In addition to the cannula mount 260, the stylet mount 262, and the trigger 288, the actuator 220 comprises a biasing member 293. According to the illustrated embodiment of the invention, the biasing member 293 is a compression spring.

The cannula 216 is generally hollow and comprises a distal end 294 defining a tip 296 and a proximal end 298 mounted to the cannula support shaft 264 of the cannula mount 260. The tip 296 is preferably pointed for insertion through skin and into the tissue mass; however, the tip 296 can optionally be blunt, for example, if the marking apparatus 210 is utilized with a probe or the like. Preferably, the cannula 216 is a 17-gage (0.058 inch outer diameter) cannula, with an inner diameter ranging from 0.049 to 0.051 inches. Furthermore, the distal end 294 of the cannula 216 can be designed for enhanced visibility using common imaging techniques, such as radiography, ultrasonography, and magnetic resonance imaging (MRI), similar to the first embodiment cannula 16. The cannula 216 slidingly receives the stylet 218, which comprises a distal end 295 located in the cannula 216 and a proximal end 297 mounted to the stylet support shaft 276 of the stylet mount 262. Prior to use of the marking device 210, the distal end 295 of the stylet 216 is spaced inwardly from the tip 296 to form a marker recess 299 for housing the imaging marker 212.

When the marking device 210 is in an assembled condition, as shown in FIG. 14, the stylet mount 262 is mounted in the hollow interior 244 adjacent the stops 245 with the stop surfaces 282 on the arms 280 abutting the stops 245 on the handle 214 to prevent proximal movement of the stylet mount 262 in the hollow interior 244. The stylet 218 extends from the stylet support shaft 270, through the cannula support shaft 264 of the cannula mount 260, which is located distally of the stylet mount 262 in the hollow interior 244, and out the distal end 232 of the handle 214 through the nose 252 of the handle cap 246. The cannula mount 260 is positioned so that the cannula 216 also leaves the distal end 232 of the handle 214 through the nose 252 of the handle cap 246. The trigger projection 292 resides in the trigger detent 272 of the cannula mount 260 to prevent proximal movement of the cannula mount 260 by the biasing member 293, which is positioned between the distal end wall 250 of the handle cap 246 and the body 266 of the cannula mount 260. The relative positioning of the cannula mount 260 and the stylet mount 262 is such that the former is spaced from the latter in the hollow interior 244, and the distal end 295 of the stylet 218 is spaced from the tip 296 to form the marker recess 299. In this condition, the cannula 216 is in an extended position where it extends from the distal end 232 of the handle 214, and the stylet 218 is in a ready position in the extended cannula 216.

Figure 15:
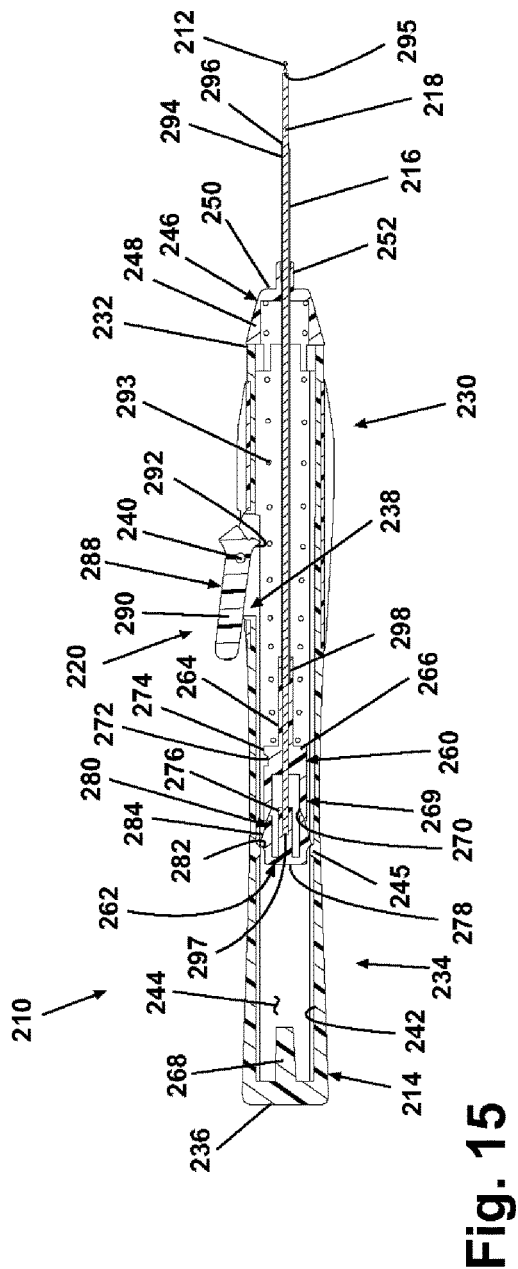
FIG. 15 is a sectional view similar to FIG. 14, with the cannula in a first retracted position to expose an imaging marker.

Referring now to FIG. 15, the cannula 216 is slidably movable in the hollow interior 244 relative to the stylet 218 in a proximal direction to expose the imaging marker 212. Retraction of the cannula 216 occurs when the projection 292 of the trigger 288 is removed from the trigger detent 272 on the cannula mount 260 by pivotal movement of the trigger finger rest 290. When the trigger 288 releases the cannula mount 260, the biasing member 293 forces the cannula mount 260 and thereby the cannula 216 proximally to a first retracted position, shown in FIG. 15, to expose the imaging marker 212.

Figure 16:
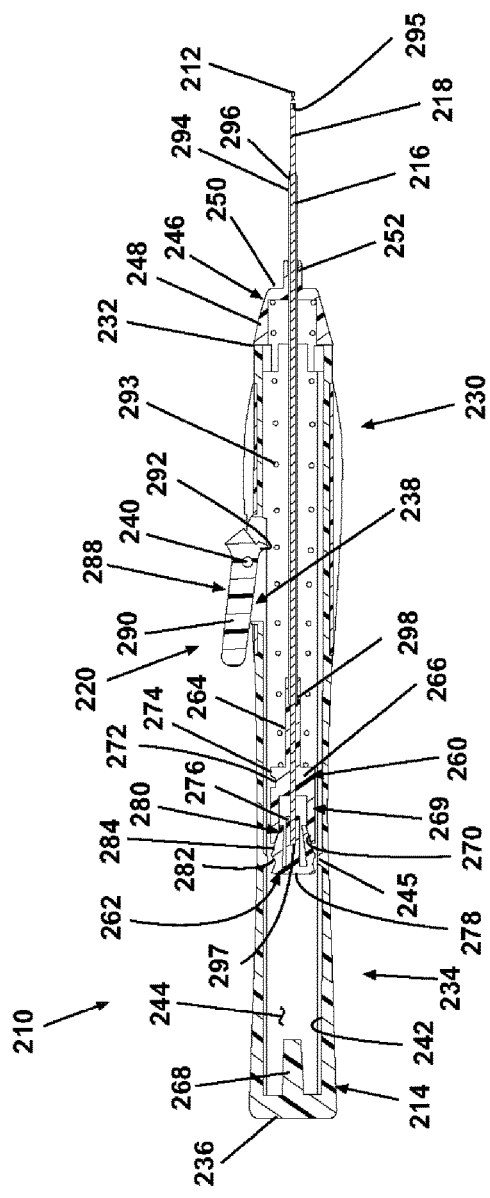
FIG. 16 is a sectional view similar to FIG. 15 with the cannula further retracted into the handle.
Figure 17:
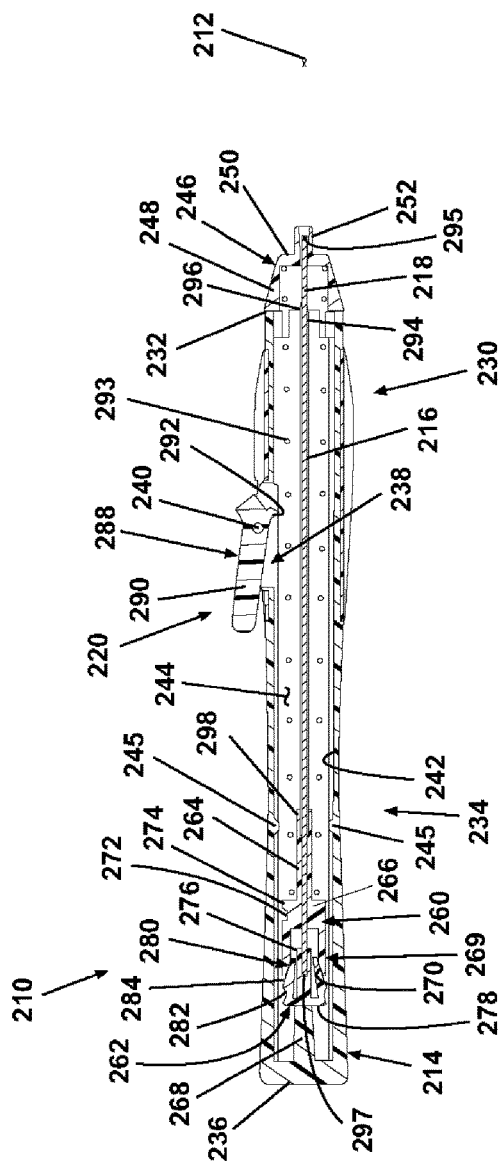
FIG. 17 is a sectional view similar to FIG. 16 with the cannula in a second retracted position and the stylet in a withdrawn position.

After exposing the imaging marker 212, the cannula 216 continues to retract into the handle 214, and the cannula mount 260 contacts the stylet mount 262, as shown in FIG. 16. In particular, the proximally extending legs 269 of the cannula mount 260 contact the distally extending arms 280 of the stylet mount 262. The cam surfaces 270 of the legs 269 contact the corresponding cam follower surfaces 284 of the arms 280 to deflect the arms 280 radially inward. As a result, the stop surfaces 282 deflect inward such that the stops 245 no longer prevent proximal movement of the stylet mount 262, and the stylet mount 262 and thereby the stylet 218 can retract with the cannula mount 260 and the cannula 218, as shown in FIG. 17. Preferably, the cannula mount 260 and the stylet mount 262 are spaced to ensure that the distal end 294 of the cannula 216 is adjacent to or extends proximally of the tip 296 for eliminating the marker recess 299 (i.e., the stylet distal end 295 is located at or extends beyond the tip 296). Thus, retraction of the stylet 218 is delayed until the cannula 218 has been sufficiently retracted relative to the stylet 218. If the marker recess 299 is present during simultaneous retraction of the cannula 216 and the stylet 218, tissue or the imaging marker 212 can potentially be undesirably drawn in to the marker recess 299.

Proximal movement of the cannula mount 260 and the stylet mount 262 retracts the cannula 216 and the stylet 218 into the hollow interior 244 to a second retracted position and a withdrawn position, respectively. Proximal movement of the cannula mount 260 and the stylet mount 262 ceases when the stylet mount 262 abuts the proximal stop 268. Preferably, when the cannula 216 is in the retracted position, the entire cannula 216, including the tip 296, is received within the handle 214. Similarly, the entire stylet 218 is preferably received within the handle 214 when in the withdrawn position, but it within the scope of the invention for the distal end 295 to project from the nose 252 when the stylet 218 is in the withdrawn position.

In operation, a practitioner grasps the marking device 210 and inserts the cannula tip 296 through the skin of patient's body into a tissue mass. The practitioner places the tip 296 typically under the guidance of aforementioned imaging systems at or near a predetermined site, such as a biopsy site. Once the cannula tip 296 is at the predetermined site, the practitioner places an index finger or other suitable finger on the finger rest 290 of the trigger 288 and pivots the trigger 288 to move the trigger 288 from a locked position of FIG. 14 to a cannula retract position of FIG. 15 to move the cannula 218 from the extended position of FIG. 14 to the first retracted position of FIG. 15, whereby the imaging marker 212 becomes exposed to the predetermined site, and the second retracted position of FIG. 17, whereby the cannula 218 retracts entirely into the handle 214. As described above, retraction of the cannula 218 from the first retracted position to the second retracted position also retracts the stylet from the ready position of FIGS. 14-16 to the withdrawn position of FIG. 17 to remove the stylet 218 along with the cannula 216 from the tissue mass as they retract into the handle 214. As in the first embodiment marking device 10, with the cannula 216 retracted into the handle 214, the practitioner cannot accidentally stab himself or herself, others assisting with the procedure, or the patient with the marking device 210 following implantation of the imaging marker 212.

While the embodiments of the marking device 10, 210 according to invention have been shown and described as comprising an actuator that automatically retracts the cannula and the stylet, such as by force of a biasing element, the actuator can alternatively move the cannula and the stylet manually. For example, the actuator can comprise a slide operably coupled to the cannula mount, and proximal movement of the slide by the user can retract the cannula and the stylet or the cannula alone into the handle. The actuator can comprise a single actuator to effect movement of the cannula and the stylet or, alternatively, individual actuators for the cannula and the stylet. Further, while the first embodiment of the marking device 10 according to invention has been shown and described as comprising an actuator that manually advances the stylet to eject the imaging marker from the marker recess, the actuator can alternatively automatically advance the stylet, such as under the force of a biasing member.

The marking device according to the invention accurately implants the imaging marker at the predetermined site and, due to the retraction of the cannula into the handle, is safe to use. With the tip of the cannula retracted into the handle, the potential for the practitioner to injure himself/herself or others is eliminated. As a result, the practitioner can focus on the implanting procedure and does not have to be concerned with safety while withdrawing the marking device from the patient. Additionally, the actuator is easy to use and facilitates accurate implantation of the imaging marker.

While the embodiments of the marking device according to the invention have been shown and described with respect to implanting a single imaging marker, it is within the scope of the invention for the marking device to implant multiple imaging markers, either at the same location or different locations in the tissue mass. Additionally, the biasing element of the actuator is not limited to a spring, as shown and described in the above embodiments. It is within the scope of the invention to employ other types of baising elements. For example, the biasing element can comprise a source of compressed gas so that the stylet is advanced with air pressure, and the cannula and the stylet are retracted with a decrease in air pressure. Another example of a biasing element is a electric coil powered by a battery, and the coil in an energized size deploys the stylet and in de-energized state retracts the cannula and the stylet.

While the invention has been specifically described in connection with certain specific embodiments thereof, it is to be understood that this is by way of illustration and not of limitation, and the scope of the appended claims should be construed as broadly as the prior art will permit.

What is claimed is:

1. A marking device, comprising:
a handle having a handle proximal end and a handle distal end and defining a hollow interior;
a cannula having a cannula distal region that includes a cannula distal end having a distal opening, the cannula being configured for slidable movement between an extended position where the cannula distal end having the distal opening extends beyond the handle distal end and a retracted position where the cannula distal end having the distal opening is received within the hollow interior;
a stylet having a stylet distal region that includes a stylet distal end, the stylet being configured for slidable movement between a ready position where the stylet distal end is proximal of the cannula distal end to form a marker recess in the cannula between the cannula distal end and the stylet distal end and an implant position where the stylet distal end extends into the marker recess to at least the distal opening in the cannula distal end;
an imaging marker located within the marker recess; and
an actuator having a cannula mount and a stylet mount, the stylet mount configured to slidably support the stylet in the handle and the cannula mount configured to slidably support the cannula in the handle, the actuator configured to define an initial condition wherein the cannula is in the extended position and the stylet is in the retracted position in the extended cannula, wherein starting from the initial condition with the cannula in the extended position, the actuator being configured to sequentially effect movement of the stylet from the ready position to the implant position to eject the imaging marker from the marker recess through the distal opening and to secure the cannula mount and a stylet mount together such that the stylet mount is fixed to the cannula mount so as to operably couple the stylet and the cannula together when the stylet is moved to the implant position, and then effect a simultaneous unitary retraction of the cannula mount, the cannula, the stylet mount, and the stylet after ejection of the imaging marker from the distal opening in the cannula distal end.

2. A marking device, comprising:
a handle having a handle proximal end and a handle distal end and defining a hollow interior;
a cannula having a cannula distal end defining an opening and having a cannula distal tip, the cannula slidably mounted to the handle, the cannula being configured for slidable movement between an extended position where the cannula distal tip extends beyond the handle distal end and a retracted position where an entirety of the cannula is received within the hollow interior;
a stylet having a stylet distal end and slidably mounted to the handle, and the stylet being configured for slidable movement between a ready position where the stylet distal end is proximal of the cannula distal end to form a marker recess in the cannula between the cannula distal end and the stylet distal end and an implant position where the stylet distal end extends into the marker recess to at least the opening in the cannula distal end;
an imaging marker located within the marker recess; and
an actuator operably coupled to the stylet and the cannula, the actuator configured to define an implant condition wherein the cannula is in the extended position and the stylet is in the implant position, wherein in a sequence beginning from the implant condition, the actuator configured to effect simultaneous retraction of the cannula and the stylet in unison to position both the cannula distal end defining the opening and the stylet distal end within the hollow interior of the handle.

3. The marking device according to claim 1, wherein during the simultaneous unitary retraction the actuator is configured to effect movement of the stylet from the implant position to a withdrawn position where the stylet distal end is received within the hollow interior of the handle.

4. The marking device according to claim 3, wherein the actuator is configured to effect the simultaneous unitary retraction of the cannula and the stylet, such that the stylet is moved from the implant position to the withdrawn position in unison with the cannula as the cannula is moved from the extended position to the retracted position.

5. The marking device according to claim 1, wherein the actuator includes a trigger and a spring biasing mechanism, the trigger being rotatably coupled to the handle, the trigger including a cam, the trigger being configured such that in a continuous rotational movement of the trigger, the cam sequentially manually moves the stylet from the ready position to the implant position to eject the imaging marker and then the cam releases the spring biasing mechanism to automatically move the cannula from the extended position to the retracted position.

6. The marking device according to claim 5, wherein the stylet is retracted in its entirety into the hollow interior of the handle when automatically moving the cannula from the extended position to the retracted position.

7. The marking device according to claim 1, wherein the actuator includes:

a cannula biasing element operably coupled with the cannula mount in the handle and configured to bias the cannula to the retracted position; and a trigger mounted to the handle and operable between a locked position and a cannula release position, wherein in the locked position the trigger prevents movement of the cannula mount and the cannula to the retracted position by the biasing element and in the cannula release position the trigger does not prevent movement of the cannula mount and the cannula to the retracted position by the biasing element.

8. The marking device according to claim 7, wherein the cannula mount is configured to support a proximal end of the cannula for sliding movement in the hollow interior and the cannula mount configured to operably couple the biasing element with the cannula.

9. The marking device according to claim 8, wherein the stylet mount is configured to support a proximal end of the stylet in the hollow interior, and further including a stylet biasing element operably coupled with the stylet mount in the hollow interior and configured to bias the stylet to the ready position.

10. The marking device according to claim 8, wherein the stylet mount is configured to support a proximal end of the stylet in the hollow interior, and wherein when the stylet mount is fixed to the cannula mount, a retraction of the cannula mount directs the stylet mount proximally in the hollow interior to move the stylet in unison with the cannula to a withdrawn position where the stylet is retracted into the hollow interior as the cannula moves to the retracted position.

11. The marking device according to claim 10, wherein the trigger includes a cam surface that rides along the stylet mount as the trigger moves from the locked position to the cannula release position to displace the stylet mount and move the stylet to the implant position to eject the imaging marker, and is configured such that thereafter the cam surface rides off the stylet mount as the trigger reaches the stylet advance position to the cannula release position to effect proximal movement of the stylet mount and the cannula mount.

12. The marking device according to claim 1 wherein the cannula distal end includes at least one imageable marking feature.

13. A marking device comprising:
a handle having a handle proximal end and a handle distal end and defining a hollow interior;
a cannula having a cannula distal end and a cannula distal tip, the cannula slidably mounted to the handle, the cannula being configured for slidable movement between an extended position where the cannula distal tip extends beyond the handle distal end and a retracted position where the cannula distal tip is received within the hollow interior;
a stylet having a stylet distal end located in the cannula proximal of the cannula distal end to form a marker recess in the cannula between the cannula distal end and the stylet distal end, the stylet having an implant position wherein the stylet distal end extends from the cannula distal end;
an imaging marker located within the marker recess; and
an actuator operably coupled to the stylet and the cannula, the actuator configured to define an implant condition wherein the cannula is in the extended position and the stylet is in the implant position, wherein in a sequence beginning from the implant condition, the actuator configured to effect simultaneous retraction of the cannula and the stylet in unison to position an entirety of both the cannula and the stylet within the hollow interior of the handle.

14. The marking device according to claim 13, wherein the actuator is configured to operably couple the stylet with the cannula when the stylet is moved to the implant position, the actuator including a trigger and a spring biasing mechanism, the trigger being rotatably coupled to the handle, the trigger including a cam, the trigger being configured such that in a continuous rotational movement of the trigger, the cam sequentially manually advances the stylet in the cannula from a ready position to the implant position to eject the imaging marker from the cannula and then the cam releases the spring biasing mechanism to automatically move the cannula from the extended position to the retracted position, the marking device being configured so that movement of the cannula to the retracted position by the spring biasing mechanism moves the stylet with the cannula to a withdrawn position where the stylet is retracted into the hollow interior.

15. The marking device according to claim 13 wherein the cannula distal end includes at least one imageable marking feature.

* * * * *